(12) United States Patent
Himmelsbach

(10) Patent No.: US 8,071,583 B2
(45) Date of Patent: Dec. 6, 2011

(54) PYRROLO[3,2-D] PYRIMIDINES AS DPP-IV INHIBITORS FOR THE TREATMENT OF DIABETES MELLITUS

(75) Inventor: Frank Himmelsbach, Mittelbiberach (DE)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 244 days.

(21) Appl. No.: 12/376,592

(22) PCT Filed: Aug. 7, 2007

(86) PCT No.: PCT/EP2007/058181
§ 371 (c)(1),
(2), (4) Date: Jun. 17, 2009

(87) PCT Pub. No.: WO2008/017670
PCT Pub. Date: Feb. 14, 2008

(65) Prior Publication Data
US 2009/0325926 A1  Dec. 31, 2009

(51) Int. Cl.
A01N 43/00 (2006.01)
A01N 43/90 (2006.01)
A61K 31/00 (2006.01)
A61K 31/519 (2006.01)
C07D 487/00 (2006.01)

(52) U.S. Cl. .................. 514/210.21; 514/265.1; 544/280

(58) Field of Classification Search .......................... None
See application file for complete search history.

(56) References Cited

U.S. PATENT DOCUMENTS

| | | | |
|---|---|---|---|
| 2,928,833 A | 3/1960 | Leake et al. | |
| 4,005,208 A | 1/1977 | Bender | |
| 4,599,338 A | 7/1986 | Regnier et al. | |
| 5,041,448 A | 8/1991 | Janssens | |
| 5,051,517 A | 9/1991 | Findeisen | |
| 5,223,499 A | 6/1993 | Greenlee | |
| 5,234,897 A | 8/1993 | Findeisen et al. | |
| 5,258,380 A | 11/1993 | Janssens | |
| 5,266,555 A | 11/1993 | Findeisen et al. | |
| 5,300,298 A | 4/1994 | LaNoue | |
| 5,332,744 A | 7/1994 | Chakravarty et al. | |
| 5,389,642 A | 2/1995 | Dorsch | |
| 5,470,579 A | 11/1995 | Bonte et al. | |
| 5,719,279 A | 2/1998 | Kufner-Muhl et al. | |
| 5,753,635 A | 5/1998 | Buckman | |
| 6,303,661 B1 | 10/2001 | Demuth | |
| 6,342,601 B1 | 1/2002 | Bantick | |
| 6,548,481 B1 | 4/2003 | Demuth et al. | |
| 6,579,868 B1 | 6/2003 | Asano | |
| 6,784,195 B2 | 8/2004 | Hale et al. | |
| 6,821,978 B2 | 11/2004 | Chackalamannil | |
| 6,869,947 B2 | 3/2005 | Kanstrup | |
| 7,060,722 B2 | 6/2006 | Kitajima | |
| 7,074,794 B2 | 7/2006 | Kitajima | |
| 7,074,798 B2 | 7/2006 | Yoshikawa | |
| 7,074,923 B2 | 7/2006 | Dahanukar | |
| 7,109,192 B2 | 9/2006 | Hauel | |
| 7,179,809 B2 | 2/2007 | Eckhardt | |
| 7,183,280 B2 | 2/2007 | Himmelsbach | |
| 7,192,952 B2 | 3/2007 | Kanstrup | |
| 7,217,711 B2 | 5/2007 | Eckhardt | |
| 7,235,538 B2 | 6/2007 | Kanstrup et al. | |
| 7,393,847 B2 | 7/2008 | Eckhardt et al. | |
| 7,407,955 B2 | 8/2008 | Himmelsbach et al. | |
| 7,432,262 B2 | 10/2008 | Eckhardt et al. | |
| 7,439,370 B2 | 10/2008 | Eckhardt | |
| 7,470,716 B2 | 12/2008 | Eckhardt et al. | |
| 7,476,671 B2 | 1/2009 | Eckhardt et al. | |
| 7,495,002 B2 | 2/2009 | Langkopf et al. | |
| 7,495,003 B2 | 2/2009 | Eckhardt et al. | |
| 7,495,005 B2 | 2/2009 | Himmelsbach et al. | |
| 7,550,455 B2 | 6/2009 | Himmelsbach et al. | |
| 7,560,450 B2 | 7/2009 | Eckhardt et al. | |
| 7,566,707 B2 | 7/2009 | Eckhardt et al. | |
| 7,569,574 B2 | 8/2009 | Maier et al. | |
| 2002/0161001 A1 | 10/2002 | Kanstrup | |

(Continued)

FOREIGN PATENT DOCUMENTS

CA    2136288 A1    5/1995

(Continued)

OTHER PUBLICATIONS

Borisy, et. al., Proceedings of the National Academy of Sciences of the United States of America, 100(13) 7977-7982.*

Augustyns, K. et al., The Unique Properties of Dipeptidyl-peptidase IV (DPP IV/CD 26) and the Therapeutic Potential of DPP-IV Inhibitors, Current Medicinal Chemistry, vol. 6, No. 4, 1999, pp. 311-327.

Beljean-Leymarie et al., Hydrazines et hydrazones hétérocycliques. IV. Synthèses de dérivés de l'hydrazine dans la série des imidazo[4,5-d]pyridazinones-4, Can. J. Chem., vol. 61, No. 11, 1983, pp. 2563-2566.

Bollag, R.J. et al; "Osteoblast-Derived Cells Express Functional Glucose-Dependent Insulinotropic Peptide Receptors," Endocrinology, vol. 141, No. 3, 2000, pp. 1228-1235.

(Continued)

*Primary Examiner* — Jeffrey Murray
(74) *Attorney, Agent, or Firm* — Michael P. Morris; Alan R. Stempel

(57) ABSTRACT

The present invention relates to substituted pyrrolo[3,2-d] pyrimidines of formula (I), wherein R1 and R2 are defined as in claim 1, including the tautomers, stereoisomers, mixtures and salts thereof, which have valuable pharmacological properties, particularly an inhibitory effect on the activity of the enzyme dipeptidylpeptidase-IV (DPP-IV).

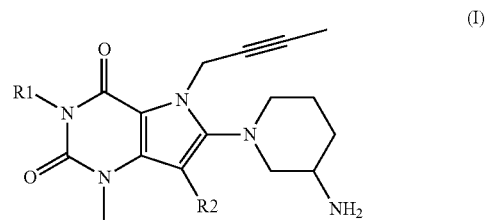

(I)

9 Claims, No Drawings

U.S. PATENT DOCUMENTS

| | | |
|---|---|---|
| 2002/0169174 A1 | 11/2002 | Chackalamannil et al. |
| 2002/0198205 A1 | 12/2002 | Himmelsbach |
| 2003/0105077 A1 | 6/2003 | Kanstrup et al. |
| 2003/0199528 A1 | 10/2003 | Kanstrup |
| 2003/0232987 A1 | 12/2003 | Dahanukar et al. |
| 2003/0236272 A1 | 12/2003 | Carr |
| 2004/0034014 A1 | 2/2004 | Kanstrup et al. |
| 2004/0077645 A1 | 4/2004 | Himmelsbach et al. |
| 2004/0082570 A1 | 4/2004 | Yoshikawa |
| 2004/0087587 A1 | 5/2004 | Himmelsbach |
| 2004/0097510 A1 | 5/2004 | Himmelsbach et al. |
| 2004/0116328 A1 | 6/2004 | Yoshikawa et al. |
| 2004/0122228 A1 | 6/2004 | Maier |
| 2004/0138214 A1 | 7/2004 | Himmelsbach et al. |
| 2004/0138215 A1 | 7/2004 | Eckhardt |
| 2004/0166125 A1 | 8/2004 | Himmelsbach |
| 2005/0020574 A1 | 1/2005 | Hauel et al. |
| 2005/0026921 A1 | 2/2005 | Eckhardt |
| 2005/0130985 A1 | 6/2005 | Himmelsbach |
| 2005/0143377 A1 | 6/2005 | Himmelsbach et al. |
| 2005/0171093 A1 | 8/2005 | Eckhardt et al. |
| 2005/0187227 A1 | 8/2005 | Himmelsbach et al. |
| 2005/0203095 A1 | 9/2005 | Eckhardt |
| 2005/0234108 A1 | 10/2005 | Himmelsbach et al. |
| 2005/0234235 A1 | 10/2005 | Eckhardt et al. |
| 2005/0261352 A1 | 11/2005 | Eckhardt |
| 2006/0004074 A1 | 1/2006 | Eckhardt |
| 2006/0058323 A1 | 3/2006 | Eckhardt et al. |
| 2006/0063787 A1 | 3/2006 | Yoshikawa |
| 2006/0079541 A1 | 4/2006 | Langkopf |
| 2006/0094722 A1 | 5/2006 | Yasuda |
| 2006/0100199 A1 | 5/2006 | Yoshikawa et al. |
| 2006/0142310 A1 | 6/2006 | Pfrengle et al. |
| 2006/0173056 A1 | 8/2006 | Kitajima |
| 2006/0205711 A1 | 9/2006 | Himmelsbach |
| 2006/0247226 A1 | 11/2006 | Himmelsbach |
| 2007/0027168 A1 | 2/2007 | Pfrengle et al. |
| 2007/0088038 A1 | 4/2007 | Eckhardt |
| 2007/0093659 A1 | 4/2007 | Bonfanti |
| 2007/0142383 A1 | 6/2007 | Eckhardt |
| 2007/0185091 A1 | 8/2007 | Himmelsbach et al. |
| 2007/0219178 A1 | 9/2007 | Muramoto |
| 2007/0259900 A1 | 11/2007 | Sieger et al. |
| 2007/0281940 A1 | 12/2007 | Dugi |
| 2008/0107731 A1 | 5/2008 | Kohlrausch et al. |
| 2008/0249089 A1 | 10/2008 | Himmelsbach et al. |
| 2008/0255159 A1 | 10/2008 | Himmelsbach et al. |
| 2008/0312243 A1 | 12/2008 | Eckhardt et al. |
| 2008/0318922 A1 | 12/2008 | Nakahira et al. |
| 2009/0023920 A1 | 1/2009 | Eckhardt |
| 2009/0088569 A1 | 4/2009 | Eckhardt et al. |
| 2009/0131432 A1 | 5/2009 | Himmelsbach et al. |
| 2009/0192314 A1 | 7/2009 | Pfrengle et al. |

FOREIGN PATENT DOCUMENTS

| | | |
|---|---|---|
| CA | 2418656 A1 | 2/2002 |
| CA | 2 496 249 A1 | 3/2004 |
| CA | 2496325 A1 | 3/2004 |
| CA | 2505389 A1 | 5/2004 |
| CA | 2508233 A1 | 6/2004 |
| CA | 2529729 A1 | 12/2004 |
| CA | 2543074 A1 | 6/2005 |
| CA | 2 555 050 A1 | 9/2005 |
| CA | 2556064 A1 | 9/2005 |
| CA | 2 590 912 A1 | 6/2006 |
| DE | 2205815 A1 | 8/1973 |
| DE | 10109021 A1 | 9/2002 |
| DE | 10117803 A1 | 10/2002 |
| EP | 0149578 A2 | 7/1985 |
| EP | 0400974 A2 | 5/1990 |
| EP | 0389282 A2 | 9/1990 |
| EP | 0399285 A1 | 11/1990 |
| EP | 0412358 A1 | 2/1991 |
| EP | 0524482 A1 | 1/1993 |
| EP | 0657454 A1 | 6/1995 |
| EP | 1054012 A1 | 11/2000 |
| EP | 1338595 A2 | 8/2003 |
| EP | 1514552 A1 | 3/2005 |
| EP | 1537880 A1 | 8/2005 |
| EP | 1 829 877 A1 | 9/2007 |
| ES | 385302 A1 | 4/1973 |
| FR | 2707641 A1 | 1/1995 |
| JP | S37-4895 | 6/1962 |
| JP | 2003/300977 | 10/2003 |
| JP | 2006/045156 | 2/2006 |
| WO | 91/07945 A1 | 6/1991 |
| WO | 92/05175 A1 | 4/1992 |
| WO | 94/03456 A1 | 2/1994 |
| WO | 96/09045 A1 | 3/1996 |
| WO | 98/11893 A1 | 3/1998 |
| WO | 99/29695 A1 | 6/1999 |
| WO | 00/73307 A2 | 12/2000 |
| WO | 02/02560 A2 | 1/2002 |
| WO | 02/14271 A1 | 2/2002 |
| WO | 02/24698 A1 | 3/2002 |
| WO | 02/068420 A1 | 9/2002 |
| WO | 03/004496 A1 | 1/2003 |
| WO | 03/024965 A2 | 3/2003 |
| WO | 03/057200 A2 | 7/2003 |
| WO | 03/104229 A1 | 12/2003 |
| WO | 2004/018467 A2 | 3/2004 |
| WO | 2004/018468 A2 | 3/2004 |
| WO | 2004/028524 A1 | 4/2004 |
| WO | 2004/033455 A2 | 4/2004 |
| WO | 2004/041820 A1 | 5/2004 |
| WO | 2004/046148 A1 | 6/2004 |
| WO | 2004/048379 A1 | 6/2004 |
| WO | 2004/050658 A1 | 6/2004 |
| WO | 2004/096806 A1 | 11/2004 |
| WO | 2004/108730 A1 | 12/2004 |
| WO | 2004/111051 A1 | 12/2004 |
| WO | 2005/058901 A1 | 6/2005 |
| WO | 2005/082906 A1 | 9/2005 |
| WO | 2005/085246 A1 | 9/2005 |
| WO | 2006/029769 A1 | 3/2006 |
| WO | 2006/048427 A1 | 5/2006 |
| WO | 2006/068163 A1 | 6/2006 |
| WO | 2007/017423 A2 | 2/2007 |
| WO | WO 2007071738 * | 6/2007 |
| WO | 2008/017670 A1 | 2/2008 |

OTHER PUBLICATIONS

Brittain, H.G., "Methods for the Characterization of Polymorphs: X-Ray Powder Diffraction," Polymorphism in Pharmaceutical Solids, 1999, p. 235-238.

Busso et al., "Circulating CD26 is Negatively Associated with Inflammation in Human and Experimental Arthritis," Am. J. Path., vol. 166, No. 2, Feb. 2005, pp. 433-442.

Caira, M.R., "Crystalline polymorphism of organic compounds" Topics in Current Chemistry, Springer, Berlin, vol. 198, 1998, p. 163-208.

Chemical Abstracts Accession No. 1987:95577: Abstract of Romanenko et al., "Synthesis and biological activity of 3-methyl, 7 -or 8-alkyl, 7,8-dialkyl, heterocyclic, and cyclohexylaminoxanthines," Farmatsevtichnii Zhurnal, 1986, (Kiev), vol. 5, 1986, pp. 41-44.

Chemical Abstracts Accession No. 106:95577 Romanenko et al., "Synthesis and biological activity of 3-methyl, 7 -or 8-alkyl-7,8-dialkyl, heterocyclic, and cyclohexylaminoxanthines," Zaporozh. Med. Institute (1986).

Conarello, S.L. et al; "Mice lacking dipeptidyl peptidase IV are protected against obesity and insulin resistance," PNAS 2003; 100:6825-6830; originally published online May 14, 2003; information current as of Dec. 2006. www.pnas.org/cgi/content/full/100/11/6825.

Cygankiewicz, Andrzej et al., Investigations into the Piperazine Derivatives of Dimethylxanthine:, Acta Polon. Pharm. [Papers of Polish Pharmacology], XXXOV, No. 5, pp. 607-612, 1977.

Deacon, C.F. et al; "Dipeptidyl peptidase IV inhabitation as an approach to the treatment and prevention of type 2 diabetes: a historical perspective;" Biochemical and Biophysical Research Communications (BBRC) 294 (2002) 1-4.

DeMeester, I. et al.; "CD26, let it cut or cut it down", Review: Immunology Today; Aug. 1999, vol. 20, No. 8 pp. 367-375.

Januvia; Patient Information; Oct. 2007.

Korom, S. et al; "Inhibition of CD26/dipeptidyl peptidase IV activity in vivo prolongs cardiac allograft survival in rat recipients[1,2]", Transplantation, May 27, 1997, vol. 63, No. 10, pp. 1495-1500.

Patani George A. et al.: "Bioisoterism : A Rational Approach in Drug Design", Chemical Reviews, 1996, vol. 96, No. 8, pp. 3147-3176.

Pospisilik, et al; Dipeptidyl Peptidase IV Inhibitor Treatment Stimulates β-Cell Survival and Islet Neogenesis in Streptozotocin-Induced Diabetic Rats; Diabetes, vol. 52, Mar. 2003 pp. 741-750.

Priimenko, B. A., et al; Synthesis and Pharmacological Activity of Derivatives of 6,8-Dimethyl Imidazo(1,2-f)Xanthine-(Russ.); Khimiko-Farmatsevticheskii Zhurnal (1984) vol. 18, No. 12 pp. 1456-1461.

Rhee et al.: "Nitrogen-15-Labeled Deoxynucleosides. 3. Synthesis of [3-$^{15}$N]-2'-Deoxyadenosine" J. Am. Chem. Soc. 1990, 112, 8174-8175.

Salomon, J., et al; Ultraviolet and γ-Ray-Induced reactions of Nucleic Acid Constituents. Reactions of Purines With Amines; Photochemistry and Photobiology (1974) vol. 19 pp. 21-27.

Sedo, A. et al; "Dipeptidyl peptidase IV activity and/or structure homologs: Contributing factors in the pathogenesis of rheumatoid arthritis?" Arthritis Research & Therapy 2005, vol. 7, pp. 253-269.

U.S. Appl. No. 12/489,716, filed Jun. 23, 2009.

Tanaka, S.. et al; "Suppression of Arthritis by the Inhibitors of Dipeptidyl Peptidase IV," In. J. Immunopharmac., vol. 19, No. 1, pp. 15-24, 1997.

Wolff, M.E.: "Burger's Medicinal Chemistry and Drug Discovery" Fifth Edition, vol. 1: Principles and Practice, pp. 975-977, 1994, John Wiley & Sons, Inc.

Yoshikawa, Seiji et al.: Chemical Abstract of Japanese Patent No. WO 2003/104229 Preparation of purinone derivatives as dipeptidylpeptidase IV (DPP-IV) inhibitors.

Zejc, Alfred et al; "Badania Nad Piperazynowymi Pochodnymi Dwumetyloksantyn" Acta Polon Pharm, XXXV, Nr. 4, 1976, pp. 417-421.

Zhong, Qing et al; "Glucose-dependent insulinotropic peptide stimulates proliferation and TGF-β release from MG-63 cells," Peptides 24 (2003) 611-616.

International Search Report for PCT/EP03/09127 mailed Nov. 28, 2003.

International Search Report for PCT/EP03/12821 mailed Mar. 30, 2004.

International Search Report for PCT/EP03/13648 mailed Apr. 5, 2004.

International Search Report for PCT/EP2007/054270 mailed Aug. 14, 2007.

International Search Report for PCT/EP2007/054204 mailed Aug. 3, 2007.

International Search Report for PCT/EP2007/054201 mailed Aug. 29, 2007.

International Search Report for PCT/EP2007/058181 mailed Nov. 28, 2007.

* cited by examiner

PYRROLO[3,2-D] PYRIMIDINES AS DPP-IV INHIBITORS FOR THE TREATMENT OF DIABETES MELLITUS

This application is the national phase entry under 35 U.S.C. §371 of International Application No. PCT/EP2007/058181, filed Aug. 7, 2007, which claims priority to European Application No. EP 06118614.4, filed Aug. 8, 2006, each of which is hereby incorporated by reference in its entirety.

The present invention relates to substituted pyrrolo[3,2-d] pyrimidines of formula (I)

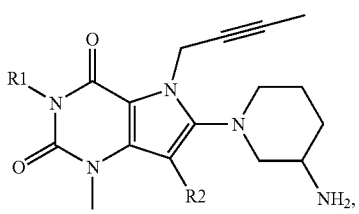

(I)

including the tautomers, enantiomers, diastereomers, mixtures and salts thereof, particularly the physiologically acceptable salts thereof with inorganic or organic acids, which have valuable pharmacological properties, particularly an inhibitory effect on the activity of the enzyme dipeptidylpeptidase-IV (DPP-IV). It describes the preparation thereof and its use for the prevention or treatment of ailments or conditions which are connected with an increased DPP-IV activity or which can be prevented or alleviated by reducing the DPP-IV activity, particularly type I or type II diabetes mellitus. For this purpose, medicaments are provided which contain a compound of formula (I) or a physiologically acceptable salt thereof.

Pyrrolo[3,2-d]pyrimidine derivatives with an inhibitory effect on DPP-IV are known from WO 06/068163.

The compounds of formula (I) shown above include the tautomers, enantiomers, diastereomers, mixtures and salts thereof wherein R1 and R2 are defined as follows:

R1 represents ([1,5]naphthyridin-2-yl)methyl, (quinazolin-2-yl)methyl], (quinoxalin-6-yl)methyl, (4-methyl-quinazolin-2-yl)methyl, 2-cyano-benzyl, (3-cyano-quinolin-2-yl)methyl, (3-cyano-pyridin-2-yl)methyl, (4-methyl-pyrimidin-2-yl)methyl, or (4,6-dimethyl-pyrimidin-2-yl)methyl and R2 represents hydrogen, methyl; hydroxy, methoxy; cyano, carboxy, methoxycarbonyl; aminocarbonyl, methylaminocarbonyl, dimethylaminocarbonyl; (2-methoxyethyl)-aminocarbonyl, (2,2,2-trifluoroethyl)aminocarbonyl; cyclopropylaminocarbonyl, cyclobutylaminocarbonyl; (cyclopropylmethyl)aminocarbonyl, (cyclobutylmethyl) aminocarbonyl; azetidin-1-ylcarbonyl, pyrrolidin-1-ylcarbonyl, piperidin-1-ylcarbonyl or morpholin-4-ylcarbonyl;

Preferred are compounds of formula (IA) or (IB)

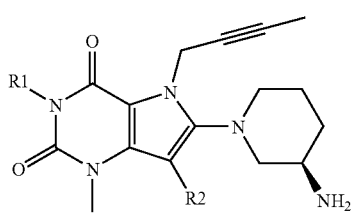

(IA)

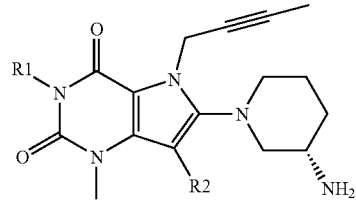

(IB)

wherein R1 and R2 are as hereinbefore defined, including the tautomers and salts thereof.

Most particularly preferred are the compounds of Example 1.

The compounds of formula (I) may be obtained by methods known per se. For example a compound of formula (II)

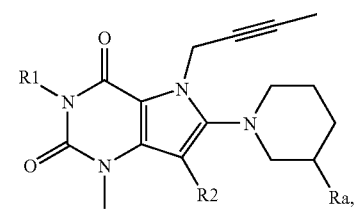

(II)

wherein R1 and R2 are as hereinbefore defined and Ra denotes an amino group protected by a protective group, is deprotected.

Preferred groups Ra are formylamino, acetylamino, trifluoroacetylamino, methoxycarbonylamino, ethoxycarbonylamino, tert.-butoxycarbonylamino and phthalimido, of which trifluoroacetylamino, methoxycarbonylamino, ethoxycarbonylamino, tert.-butoxycarbonylamino and phthalimido are particularly preferred.

The cleaving of a tert.-butyloxycarbonyl group is preferably carried out by treating with an acid such as trifluoroacetic acid or hydrochloric acid, optionally using a solvent such as methylene chloride, dioxane, methanol, ethanol, isopropanol or diethyl ether.

A formyl, acetyl, methoxycarbonyl, ethoxycarbonyl or trifluoroacetyl group is preferably cleaved by treating with an acid such as hydrochloric acid, optionally in the presence of a solvent such as acetic acid, at temperatures between 20 and 120° C. or by treating with sodium hydroxide solution, optionally in the presence of a solvent such as tetrahydrofuran, methanol or ethanol, at temperatures between 0 and 100° C.

A phthaloyl group is preferably cleaved in the presence of hydrazine or a primary amine such as methylamine, ethylamine, ethanolamine or n-butylamine in a solvent such as methanol, ethanol, isopropanol, toluene/water or dioxane at temperatures between 20° C. and the reflux temperature of the reaction mixture.

The invention further relates to the intermediate products of formula (II), particularly those of formula (IIA) and (IIB)

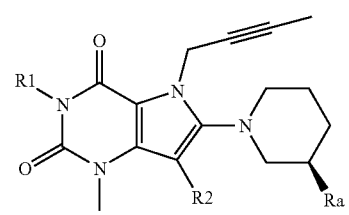

(IIA)

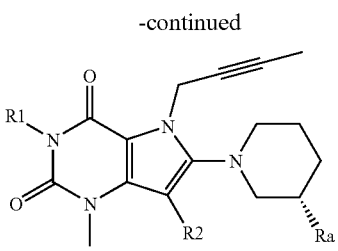

(IIB)

as shown, wherein R1, R2 and Ra are as hereinbefore defined.

The compounds of formula (I) obtained may be separated into the enantiomers and/or diastereomers thereof. Thus, for example, cis-/trans mixtures may be separated into their cis and trans isomers, and compounds with at least one optically active carbon atom may be resolved into their enantiomers.

Thus, for example, cis-/trans mixtures obtained may be separated by chromatography into their cis and trans isomers and the compounds of formula (I) obtained which occur as racemates may be separated by methods known per se (cf. Allinger N. L. and Eliel E. L. in "Topics in Stereochemistry", Vol. 6, Wiley Interscience, 1971) into their optical antipodes. Compounds of formula (I) with at least 2 asymmetric carbon atoms may be resolved into their diastereomers on the basis of their physical-chemical differences using methods known per se, e.g. by chromatography and/or fractional crystallization, and, if these compounds are obtained in racemic form, they may subsequently be resolved into the enantiomers as mentioned above.

The enantiomers are preferably separated by column separation on chiral phases or by recrystallization from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be, for example, (+) or (−)-menthol and an optically active acyl group in amides, for example, may be a (+)- or (−)-menthyloxycarbonyl.

Furthermore, compounds of formula (I) may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

The compounds of formula (II) used as starting materials are either known from the literature or are obtained by methods such as those described for example in WO 04/018468, WO 05/085246 or WO 06/068163.

The compounds of formula (I) according to the invention and the physiologically acceptable salts thereof have valuable pharmacological properties, particularly an inhibiting effect on the enzyme DPP-IV. The ability of the substances including their salts to inhibit the DPP-IV activity can be demonstrated in an experiment in which an extract of the human colon carcinoma cell line Caco-2 is used as the DPP IV source. The differentiation of the cells in order to induce the DPP-IV expression is carried out in accordance with the description by Reiher et al. in an article entitled "Increased expression of intestinal cell line Caco-2", which appeared in Proc. Natl. Acad. Sci. Vol. 90, pp. 5757-5761 (1993). The cell extract is obtained from cells solubilized in a buffer (10 mM Tris HCl, 0.15 M NaCl, 0.04 t.i.u. aprotinin, 0.5% Nonidet-P40, pH 8.0) by centrifugation at 35,000 g for 30 minutes at 4° C. (to remove cell debris).

The DPP-IV assay is carried out as follows:

50 µl of substrate solution (amido-4-trifluoromethylcoumarin (AFC)), final concentration 100 µM, are placed in black microtitre plates. 20 µl of assay buffer (final concentrations 50 mM Tris HCl pH 7.8, 50 mM NaCl, 1% DMSO) is pipetted in. The reaction is started by the addition of 30 µl of solubilized Caco-2 protein (final concentration 0.14 µg of protein per well). The test substances under investigation are typically added prediluted to 20 µl, while the volume of assay buffer is then reduced accordingly. The reaction is carried out at ambient temperature, the incubation period is 60 minutes. Then the fluorescence is measured in a Victor 1420 Multilabel Counter, with the excitation wavelength at 405 nm and the emission wavelength at 535 nm. Dummy values (corresponding to 0% activity) are obtained in mixtures with no Caco-2 protein (volume replaced by assay buffer), control values (corresponding to 100% activity) are obtained in mixtures without any added substance. The potency of a test substance, expressed as the $IC_{50}$ value, is calculated from dosage/activity curves consisting of 11 measured points in each case.

In view of their ability to inhibit DPP-IV activity, the compounds of formula (I) according to the invention and the corresponding pharmaceutically acceptable salts thereof are suitable for influencing any conditions or ailments which can be affected by the inhibition of the DPP-IV activity. It is therefore to be expected that the compounds according to the invention will be suitable for the prevention or treatment of diseases or conditions such as type I and type 11 diabetes mellitus, prediabetes, reduced glucose tolerance or changes in the fasting blood sugar, diabetic complications (e.g. retinopathy, nephropathy or neuropathies), metabolic acidosis or ketosis, reactive hypoglycaemia, insulin resistance, metabolic syndrome, dyslipidaemias of various origins, arthritis, atherosclerosis and related diseases, obesity, allograft transplantation and osteoporosis caused by calcitonin. In addition, these substances are suitable for preventing B-cell degeneration such as e.g. apoptosis or necrosis of pancreatic B-cells. The substances are also suitable for improving or restoring the function of pancreatic cells and additionally increasing the size and number of pancreatic B-cells. Additionally, on the basis of the role of the glucagon-like peptides such as e.g. GLP-1 and GLP-2 and their link with DPP-IV inhibition, it is expected that the compounds according to the invention will be suitable for achieving a sedative or tranquilizing effect, as well as having a favourable effect on catabolic states after operations or hormonal stress responses or possibly reducing mortality and morbidity after myocardial infarction. Moreover, they are suitable for treating any conditions connected with the effects mentioned above and mediated by GLP-1 or GLP-2. The compounds according to the invention may also be used as diuretics or antihypertensives and are suitable for preventing and treating acute kidney failure. The compounds according to the invention may also be used to treat inflammatory complaints of the respiratory tract. They are also suitable for preventing and treating chronic inflammatory bowel diseases such as e.g. irritable bowel syndrome (IBS), Crohn's disease or ulcerative colitis and also pancreatitis. It is also expected that they can be used for all kinds of injury or damage to the gastrointestinal tract such as may occur in colitis and enteritis, for example. Moreover, it is expected that DPP-IV inhibitors and hence the compounds according to the invention can be used to treat infertility or to improve fertility in humans or mammals, particularly if the infertility is connected with insulin resistance or with polycystic ovary syndrome. On the other hand these substances are suitable for influencing sperm motility and are thus suitable for use as male contraceptives. In addition, the substances are suitable for treating growth hormone deficiencies connected with restricted growth, and may reasonably be used for all indications for which growth hormone may be used. The compounds according to the invention are also suitable, on the basis of their inhibitory effect on DPP-IV, for treating various autoimmune diseases such as e.g. rheumatoid arthritis, multiple sclerosis, thyroiditis and Basedow's disease, etc. They may also be used to treat viral diseases and also, for example, in HIV infections, for stimulating blood production, in benign prostatic hyperplasia, gingivitis, as well as for the treatment of neuronal defects and neuro-degenerative diseases such as Alzheimer's disease, for example. The compounds described may also be used for the treatment of tumours, particularly for modifying tumour invasion and also metastasisation; examples here are their use in treating T-cell lymphomas, acute lymphoblastic leukaemia, cell-based thyroid carcinomas, basal cell carcinomas or breast cancers. Other indications are stroke, ischaemia of various origins, Parkinson's disease and migraine. In addition, further indications include follicular and epidermal hyperkeratoses, increased keratinocyte proliferation, psoriasis, encephalomyelitis, glomerulonephritis, lipodystrophies, as well as psycho-somatic, depressive and neuropsychiatric diseases of all kinds.

The compounds according to the invention may also be used in conjunction with other active substances. Suitable therapeutic agents for such combinations include for example antidiabetic agents such as metformin, sulphonylureas (e.g. glibenclamide, tolbutamide, glimepiride), nateglinide, repaglinide, thiazolidinediones (e.g. rosiglitazone, pioglitazone), PPAR-gamma agonists (e.g. GI 262570) and antagonists, PPAR-gamma/alpha modulators (e.g. KRP 297), PPAR-gamma/alpha/delta modulators, AMPK activators, ACC1 and ACC2 inhibitors, DGAT-inhibitors, SMT3 receptor agonists, 11β-HSD inhibitors, FGF19 agonists or mimetics, alpha-glucosidase inhibitors (e.g. acarbose, voglibose), other DPPIV inhibitors, alpha2 antagonists, insulin and insulin analogues, GLP-1 and GLP-1 analogues (e.g. exendin-4) or amylin. Also, combinations with SGLT2 inhibitors such as T-1095 or KGT-1251 (869682), inhibitors of protein tyrosine phosphatase 1, substances which influence deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, lipid lowering agents, such as HMG-CoA-reductase inhibitors (e.g. simvastatin, atorvastatin), fibrates (e.g. bezafibrate, fenofibrate), nicotinic acid and its derivatives, PPAR-alpha agonists, PPAR-delta agonists, ACAT inhibitors (e.g. avasimibe) or cholesterol absorption inhibitors such as for example ezetimibe, bile acid-binding substances such as for example cholestyramine, inhibitors of ileac bile acid transport, HDL-raising compounds such as for example inhibitors of CETP or regulators of ABC1 or LXRalpha antagonists, LXRbeta agonists or LXRalpha/beta regulators or active substances for the treatment of obesity, such as e.g. sibutramine or tetrahydrolipostatin, dexfenfluramine, axokine, antagonists of the cannabinoid1 receptor, MCH-1 receptor antagonists, MC4 receptor agonists, NPY5 or NPY2 antagonists or β$_3$-agonists such as SB-418790 or AD-9677 as well as agonists of the 5HT2c receptor, are possible.

It is also possible to combine the compounds with drugs for treating high blood pressure such as e.g. all antagonists or ACE inhibitors, diuretics, β-blockers, Ca-antagonists, etc., or combinations thereof.

The dosage required to expediently achieve such an effect is, by intravenous route, 1 to 100 mg, preferably 1 to 30 mg, and by oral route 1 to 1000 mg, preferably 1 to 100 mg, in each case 1 to 4 times a day. For this purpose, the compounds of formula I prepared according to the invention, optionally combined with other active substances, may be incorporated together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof into conventional galenic preparations such as plain or coated tablets, capsules, powders, suspensions or suppositories.

The Examples that follow are intended to illustrate the invention:

EXAMPLE 1

1-methyl-3-[(quinazolin-2-yl)methyl]-5-(2-butyn-1-yl)-6-(3-(R)-amino-piperidin-1-yl)-7-cyano-2,4-dioxo-2.3.4,5-tetrahydro-1H-pyrrolo[3,2-d]pyrimidine The title compound may be obtained by reacting 1-methyl-3-[(quinazolin-2-yl)methyl]-5-(2-butyn-1-yl)-6-[3-(R)-(tert.-butyloxycarbonylamino)-piperidin-1-yl]-7-cyano-2,4-dioxo-2,3,4,5-tetrahydro-1H-pyrrolo[3,2-d]pyrimidine with isopropanolic hydrochloric acid.

The following may be obtained analogously to Example 1 and other methods known from the literature:

| Compound | Structure |
|---|---|
| (1) | 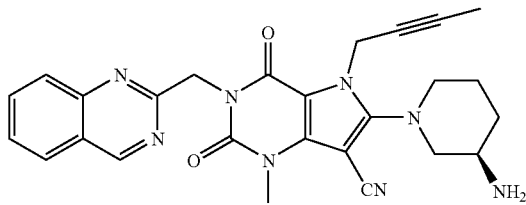 |

| Compound | Structure |
|---|---|
| (2) | 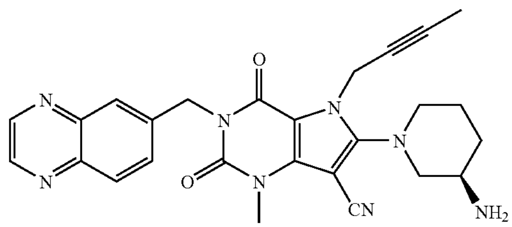 |
| (3) | 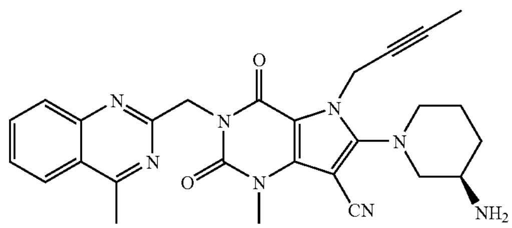 |
| (4) | 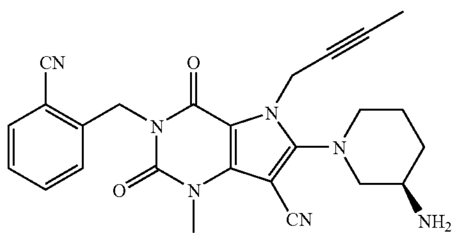 |
| (5) | 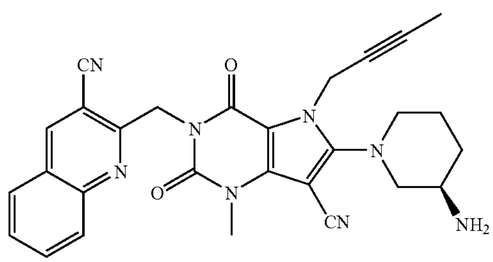 |
| (6) | 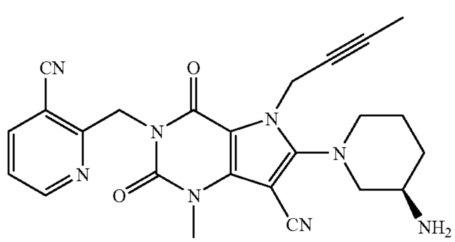 |
| (7) | 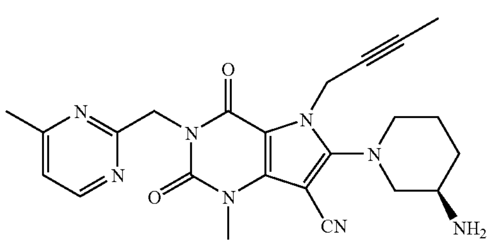 |
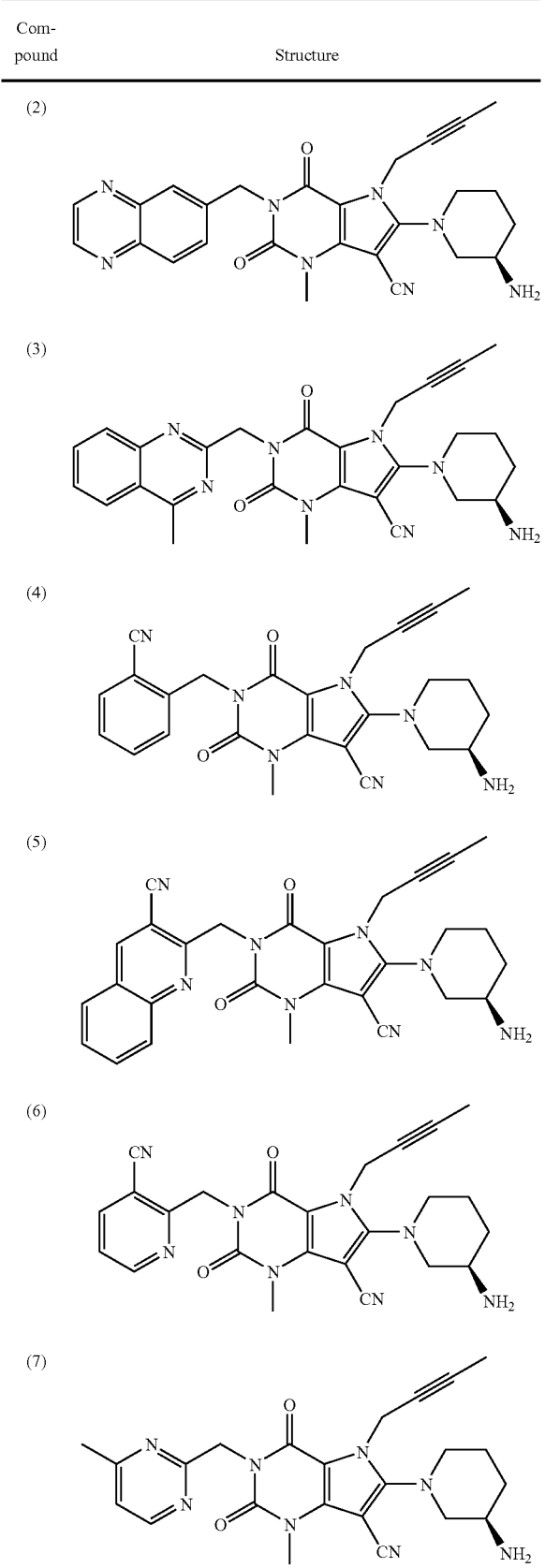
| Compound | Structure |
|---|---|
| (8) | 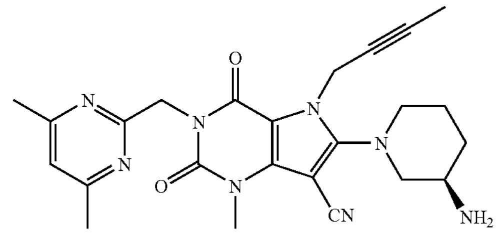 |
| (9) | 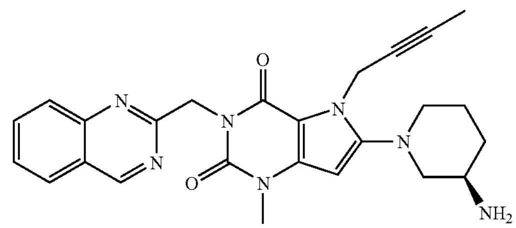 |
| (10) | 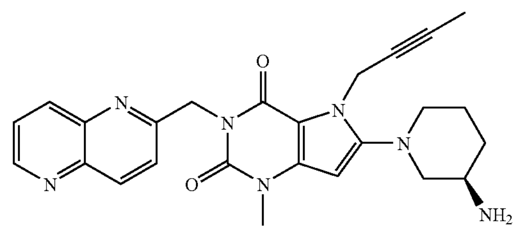 |
| (11) | 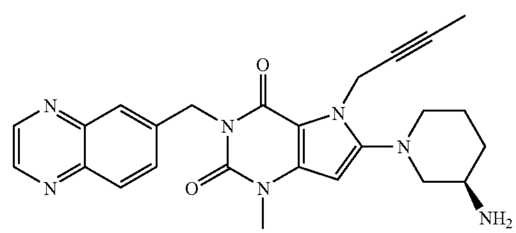 |
| (12) | 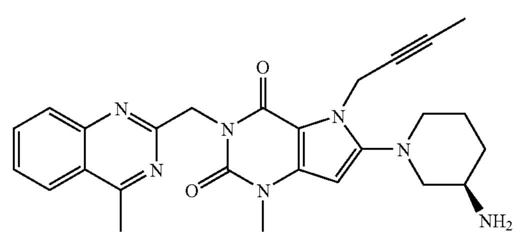 |
| (13) | 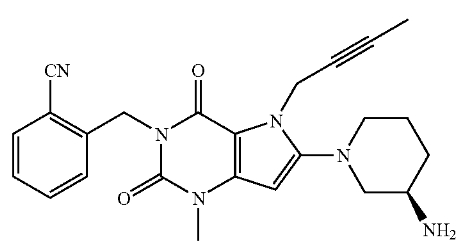 |
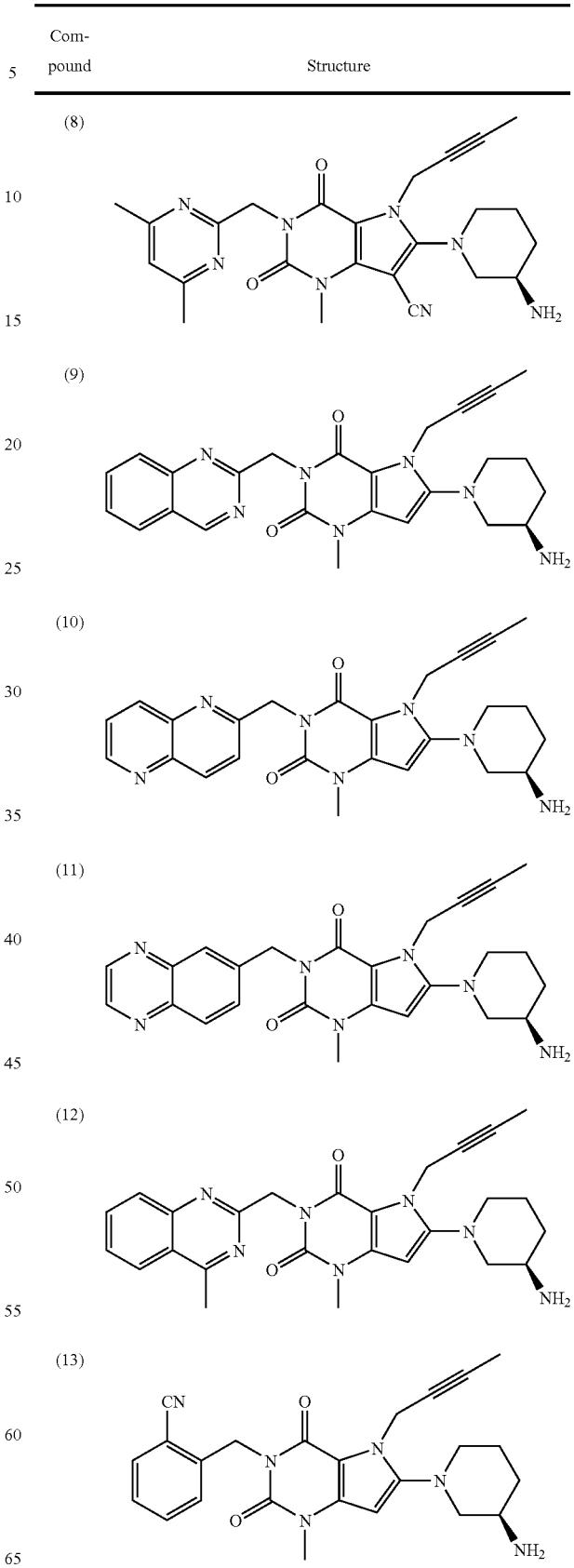

| Compound | Structure |
|---|---|
| (14) | 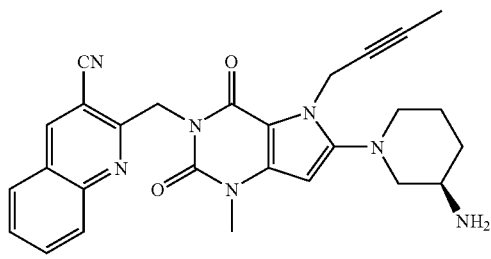 |
| (15) | 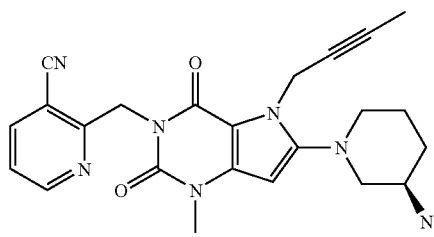 |
| (16) | 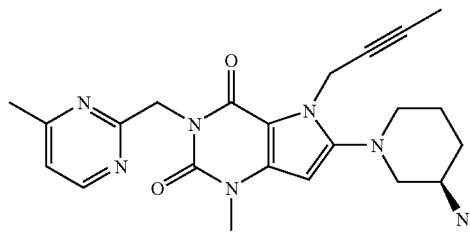 |
| (17) | 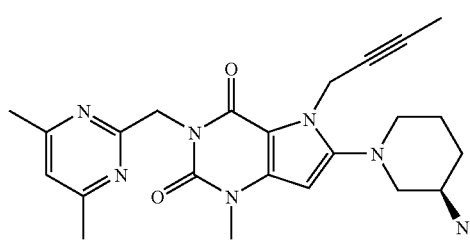 |
| (18) | 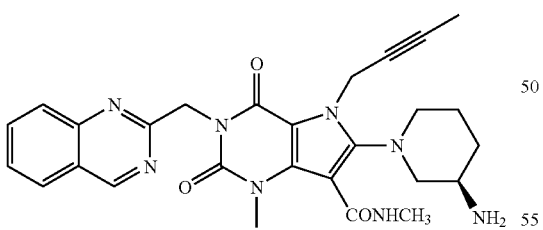 |
| (19) | 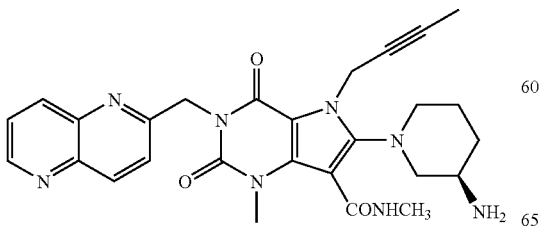 |
| Compound | Structure |
|---|---|
| (20) | 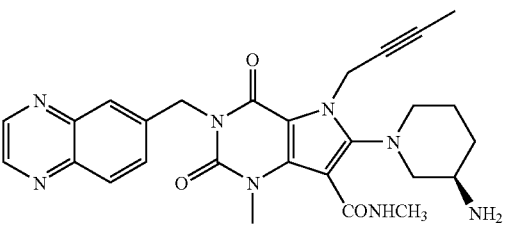 |
| (21) | 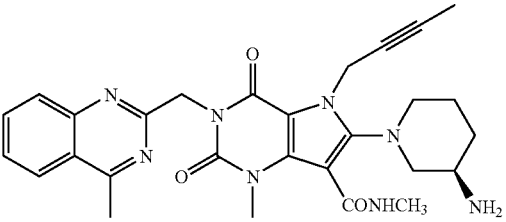 |
| (22) | 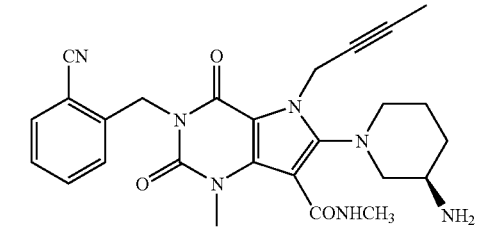 |
| (23) | 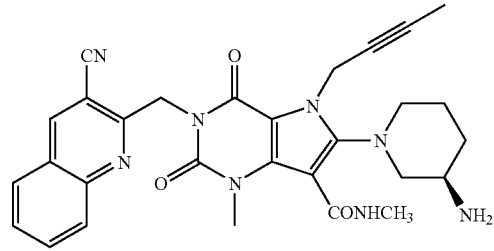 |
| (24) | 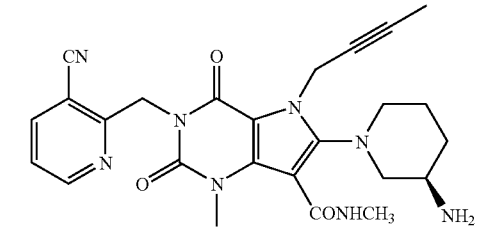 |
| (25) | 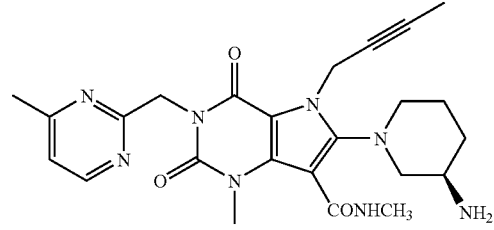 |

| Compound | Structure |
|---|---|
| (26) | 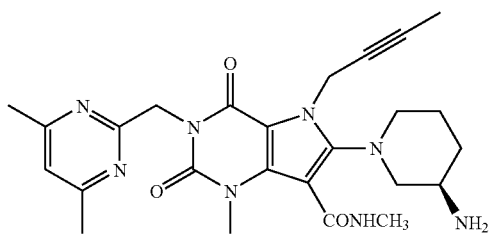 |
| (27) | 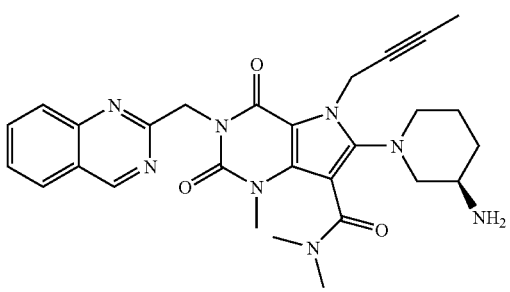 |
| (28) | 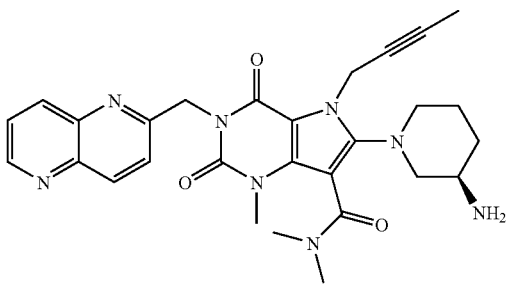 |
| (29) | 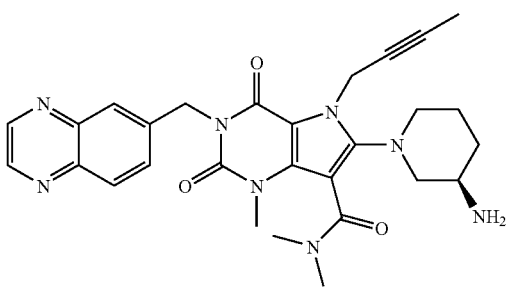 |
| (30) | 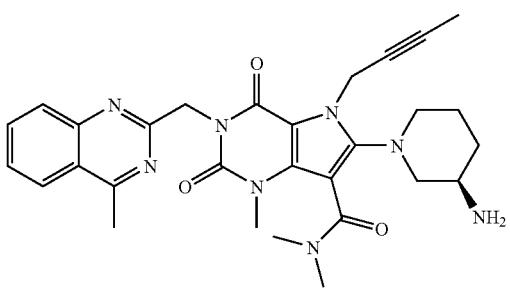 |
| Compound | Structure |
|---|---|
| (31) | 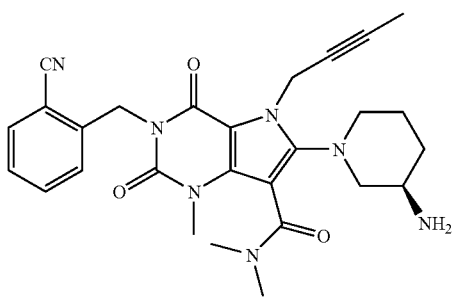 |
| (32) | 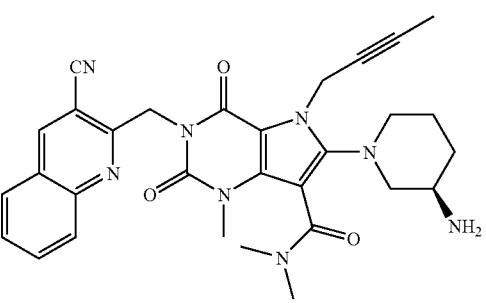 |
| (33) | 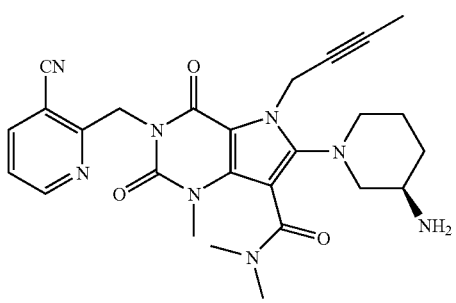 |
| (34) | 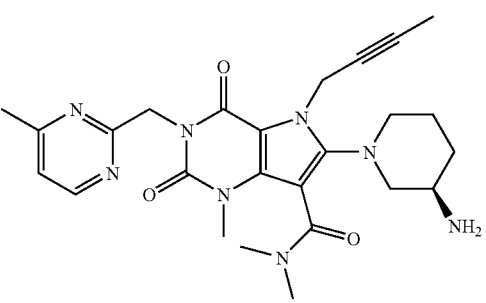 |
| (35) | 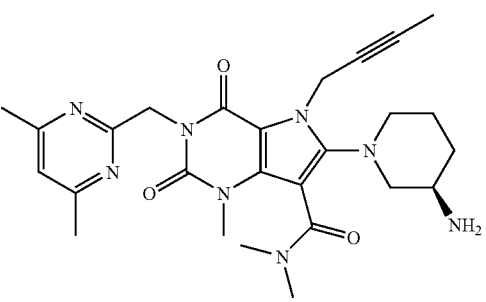 |

| Compound | Structure |
|---|---|
| (36) | 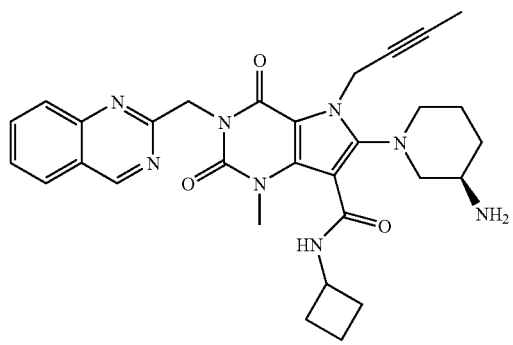 |
| (37) | 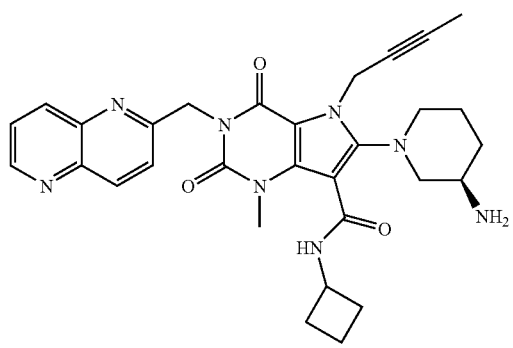 |
| (38) | 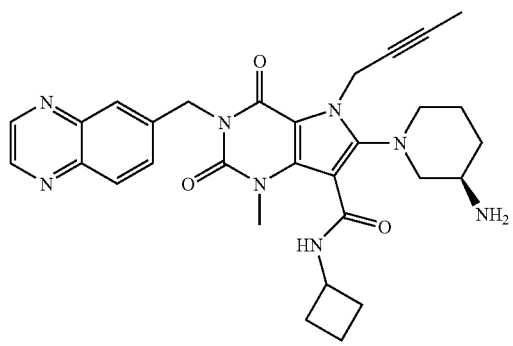 |
| (39) | 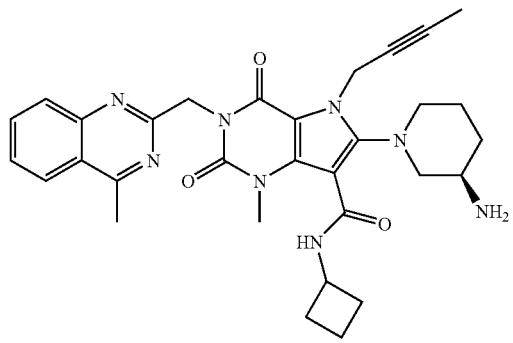 |
| (40) | 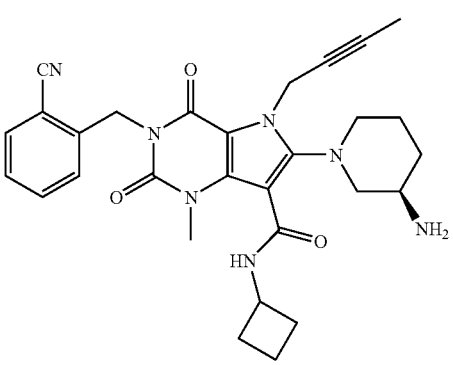 |
| (41) | 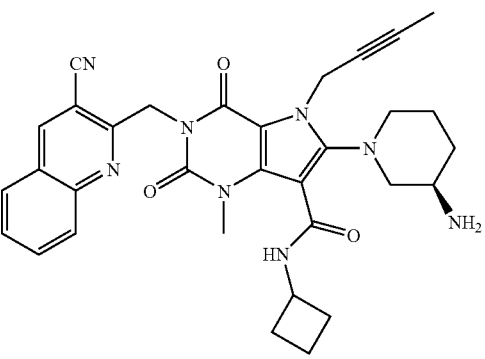 |
| (42) | 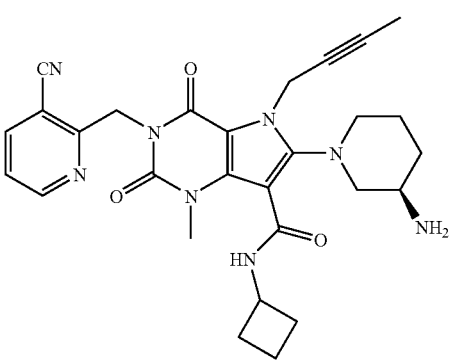 |
| (43) | 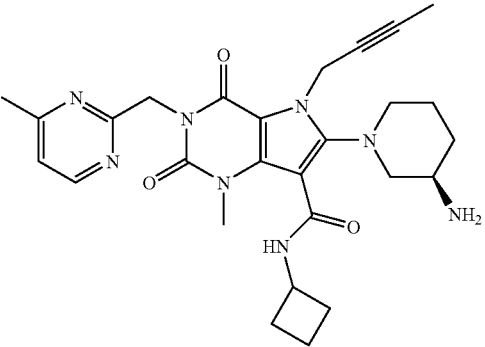 |

-continued
| Compound | Structure |
|---|---|
| (44) | 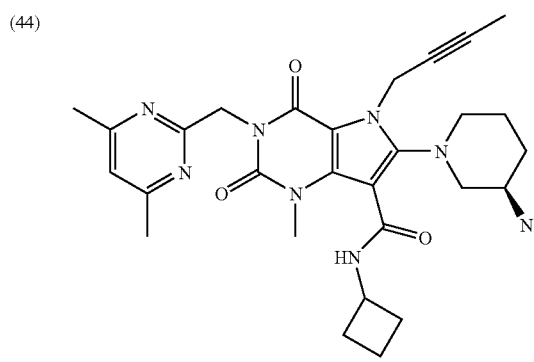 |
| (45) | 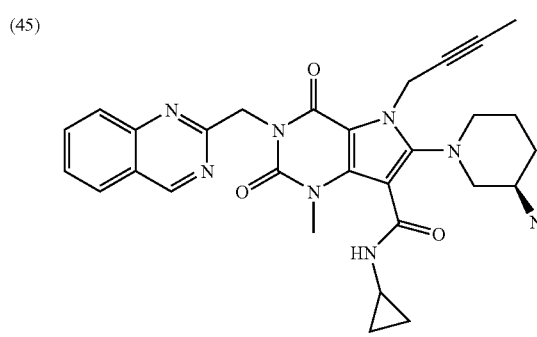 |
| (46) | 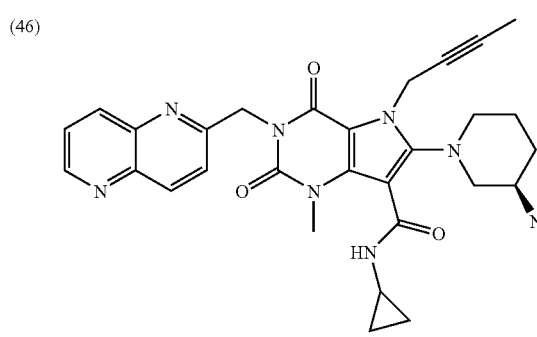 |
| (47) | 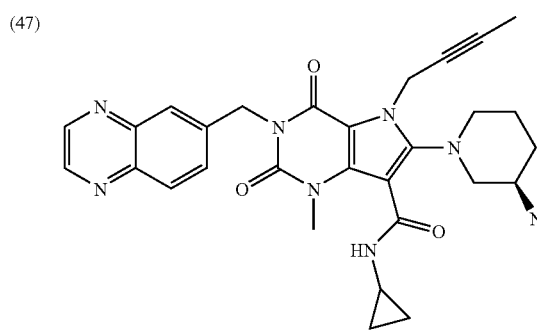 |
-continued
| Compound | Structure |
|---|---|
| (48) | 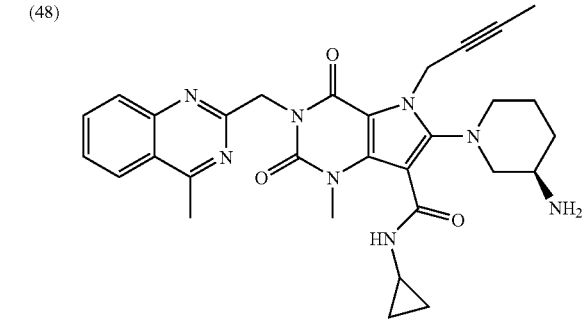 |
| (49) | 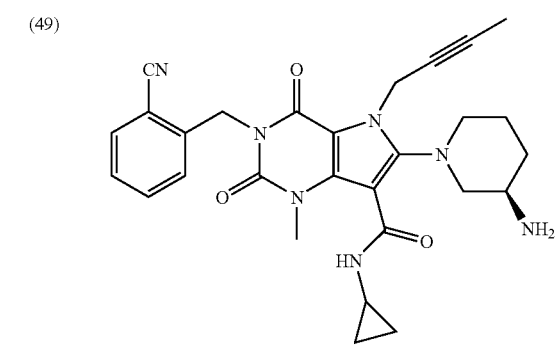 |
| (50) | 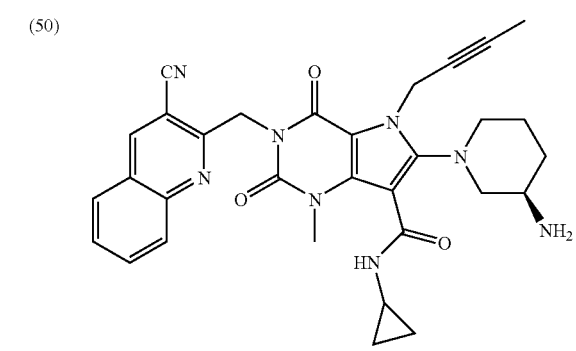 |
| (51) | 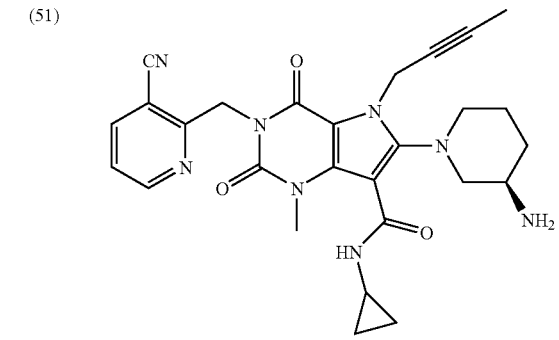 |

| Compound | Structure |
|---|---|
| (52) | 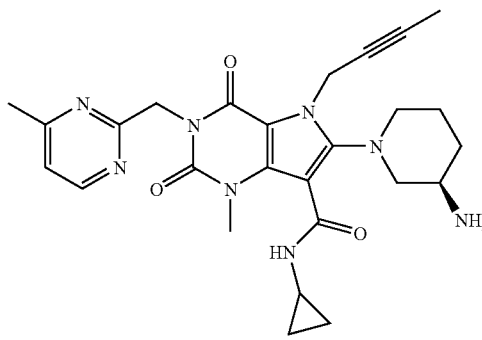 |
| (53) | 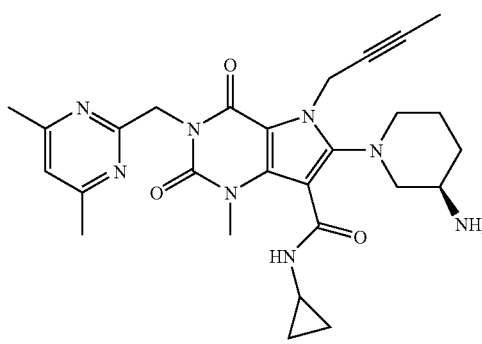 |
| (54) | 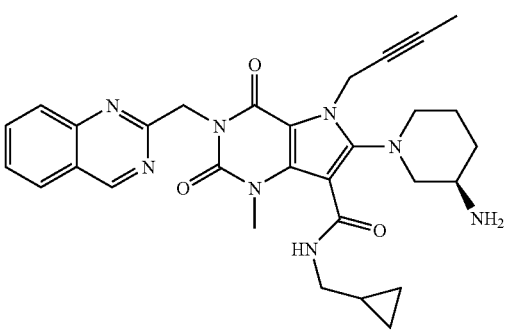 |
| (55) | 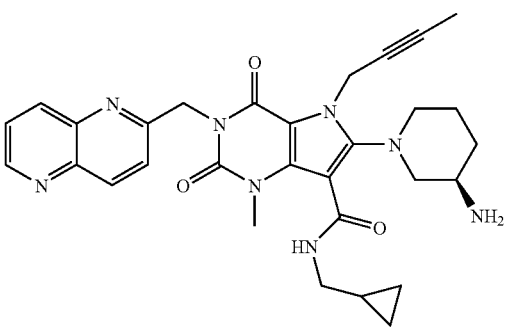 |
| Compound | Structure |
|---|---|
| (56) | 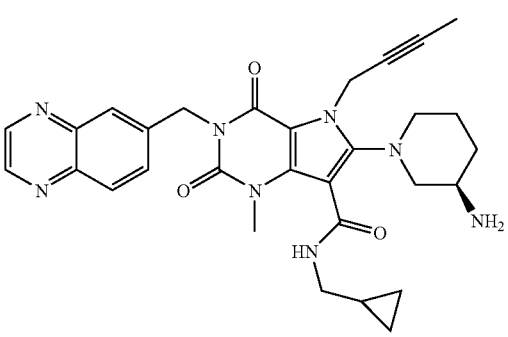 |
| (57) | 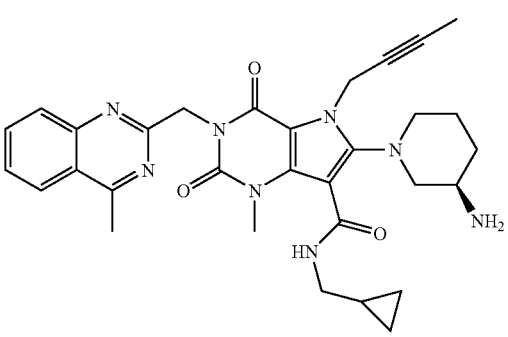 |
| (58) | 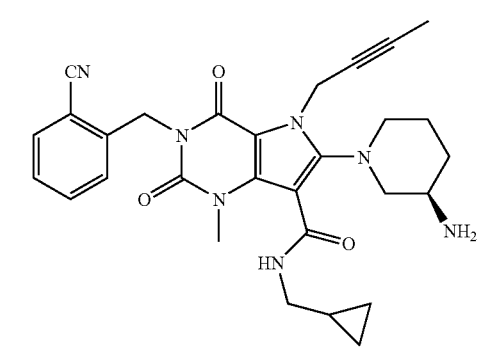 |
| (59) | 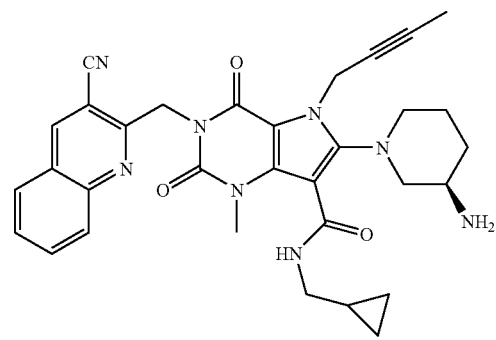 |

| Compound | Structure |
|---|---|
| (60) | 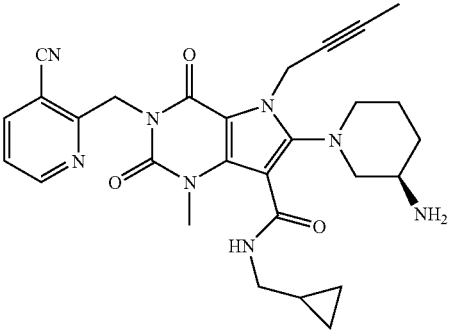 |
| (61) | 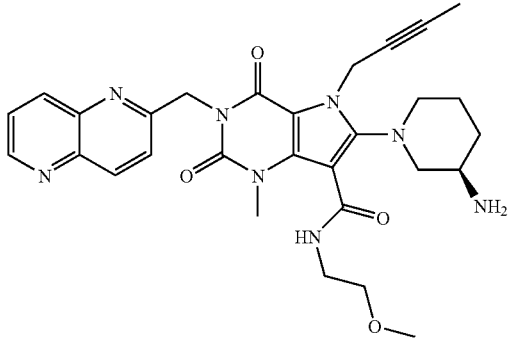 |
| (62) | 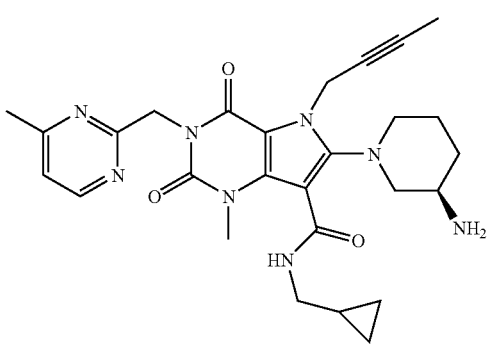 |
| (63) | 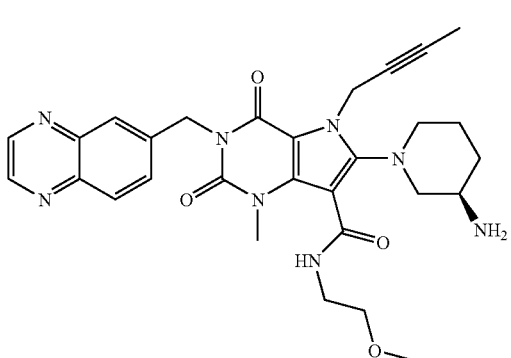 |
| (64) | 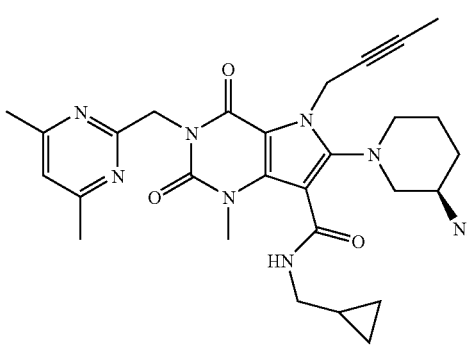 |
| (65) | 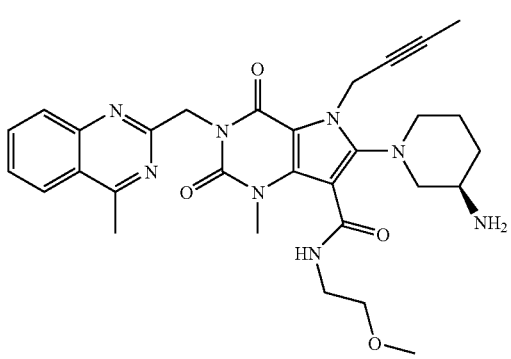 |
| (66) | 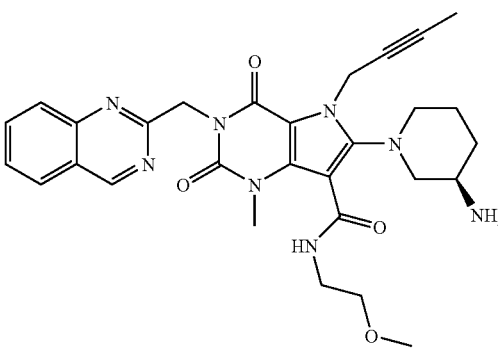 |
| (67) | 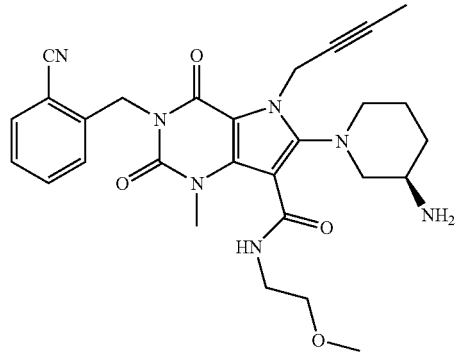 |

| Compound | Structure |
|---|---|
| (68) | 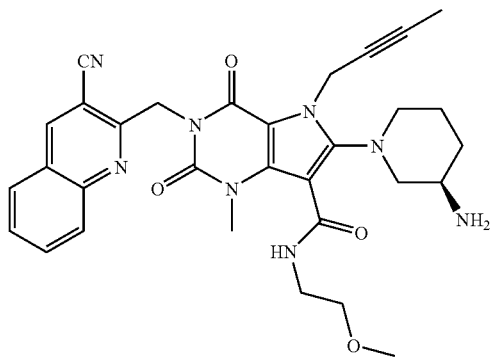 |
| (69) | 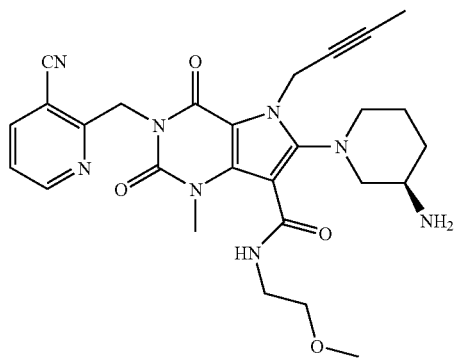 |
| (70) | 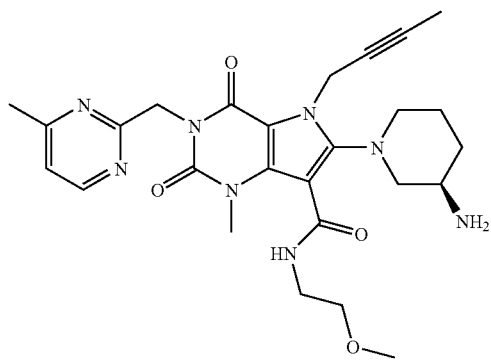 |
| (71) | 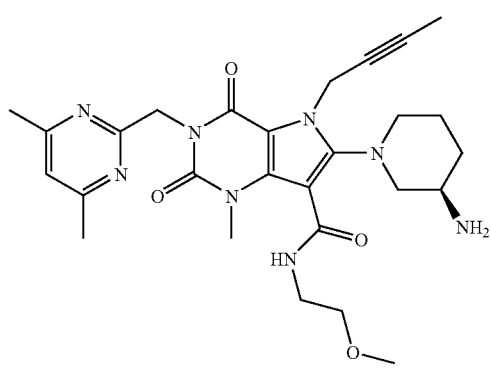 |
| Compound | Structure |
|---|---|
| (72) | 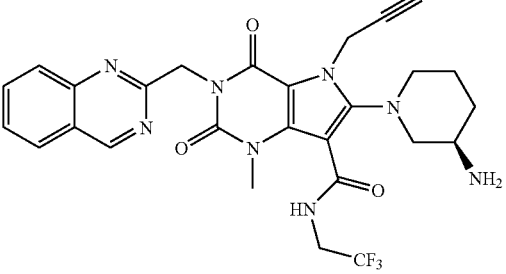 |
| (73) | 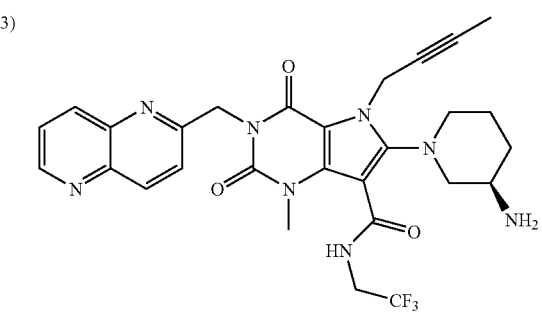 |
| (74) | 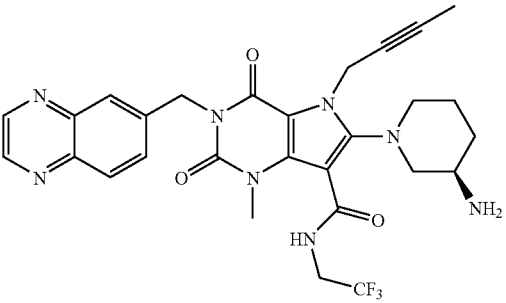 |
| (75) | 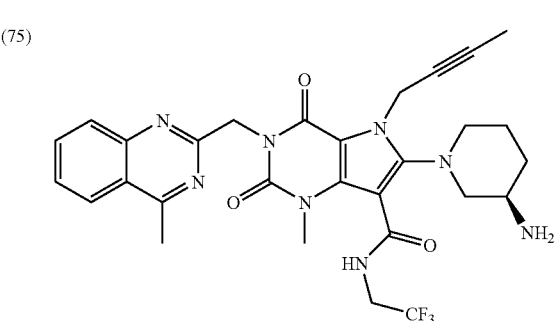 |
| (76) | 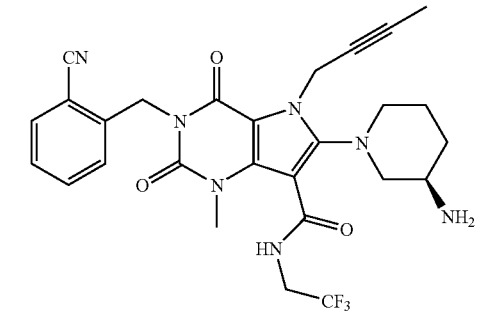 |

-continued
| Compound | Structure |
|---|---|
| (77) | 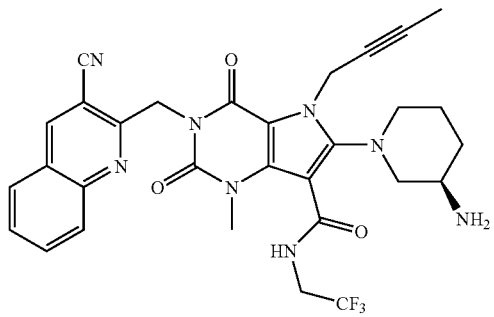 |
| (78) | 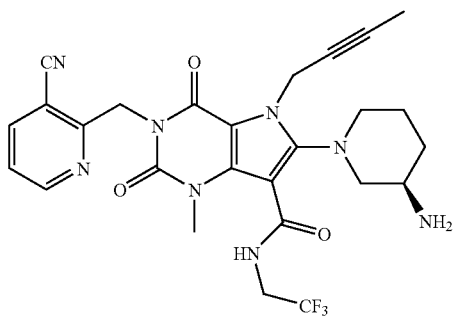 |
| (79) | 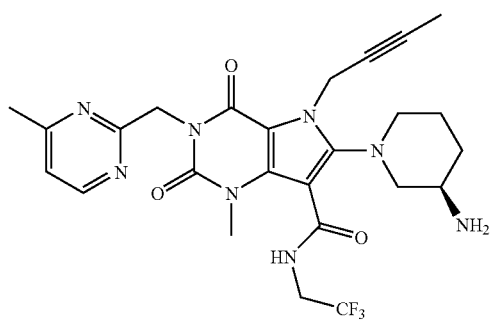 |
| (80) | 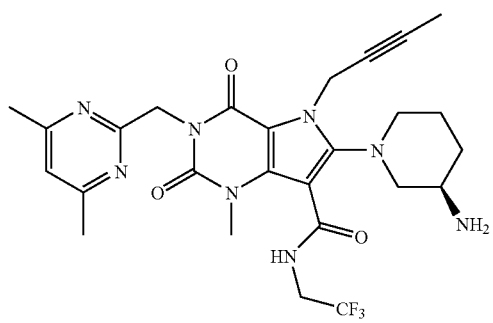 |
-continued
| Compound | Structure |
|---|---|
| (81) | 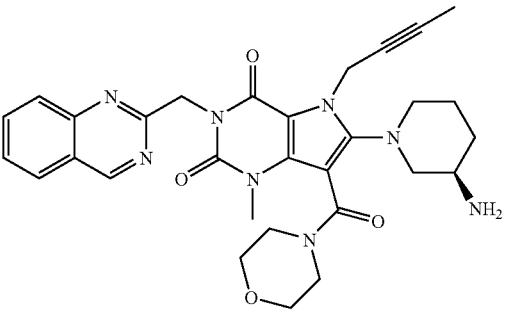 |
| (82) | 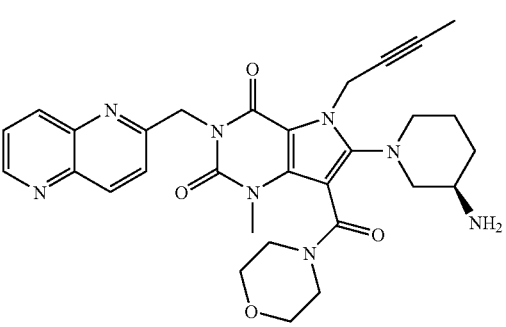 |
| (83) | 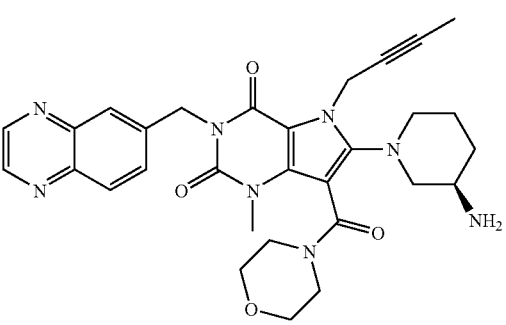 |
| (84) | 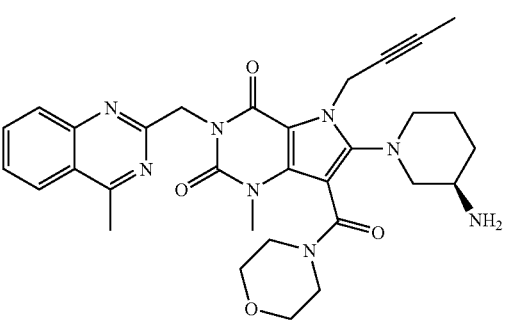 |

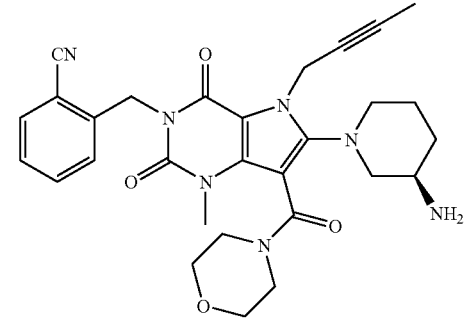

| Compound | Structure |
|---|---|
| (95) | 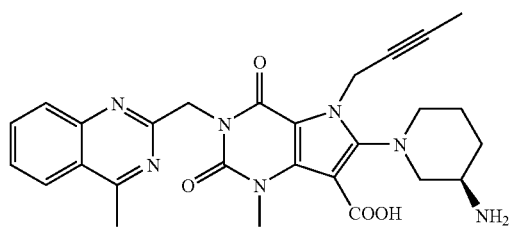 |
| (96) | 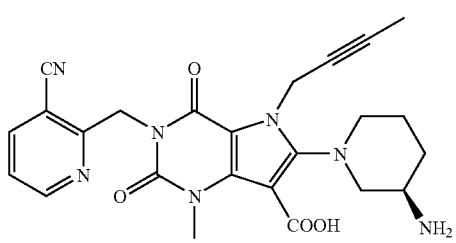 |
| (97) | 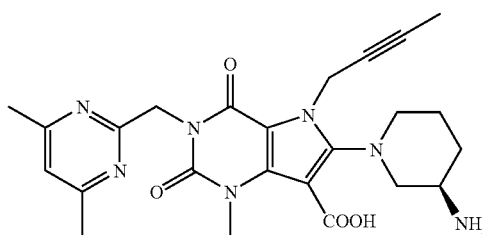 |
| (98) | 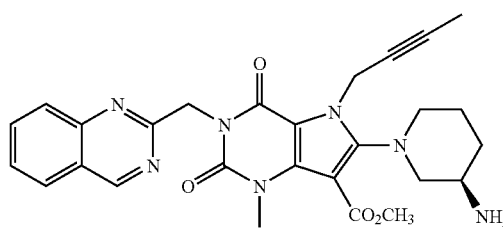 |
| (99) | 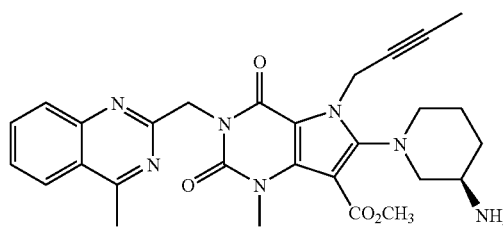 |
| (100) | 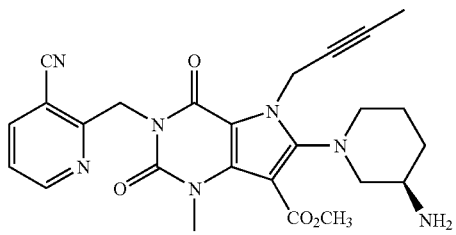 |
| Compound | Structure |
|---|---|
| (101) | 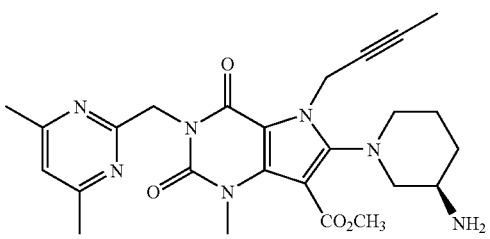 |
| (102) | 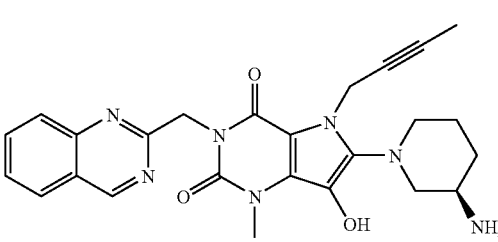 |
| (103) | 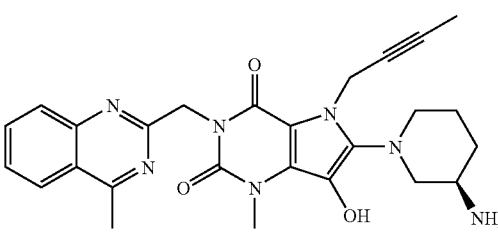 |
| (104) | 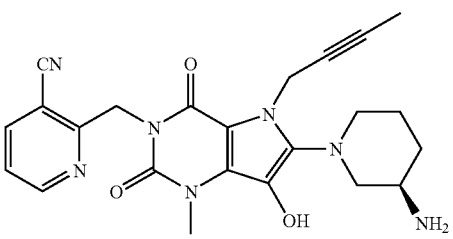 |
| (105) | 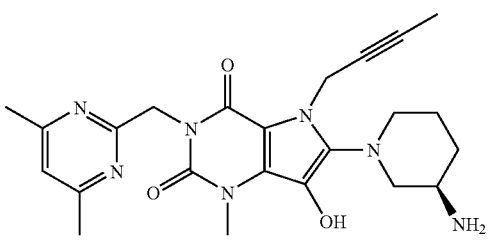 |
| (106) | 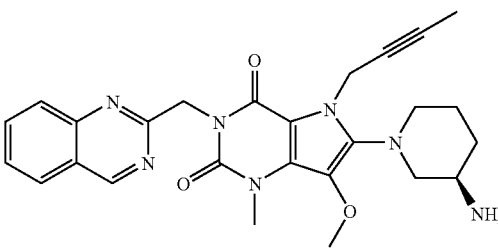 |

| Compound | Structure |
|---|---|
| (107) | 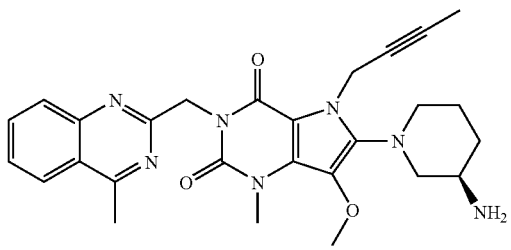 |
| (108) | 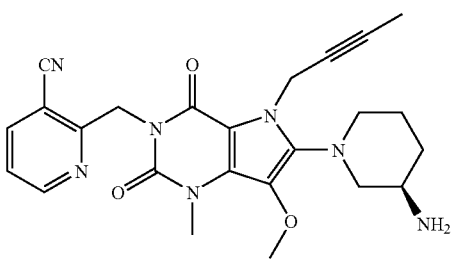 |
| (109) | 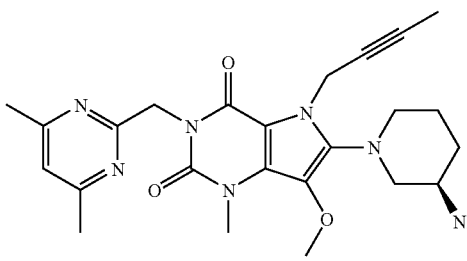 |
| (110) | 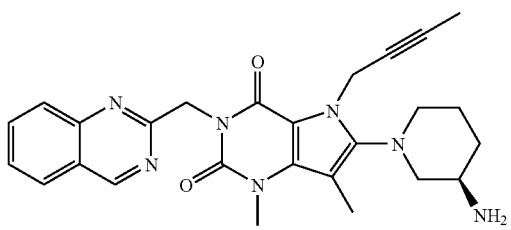 |
| (111) | 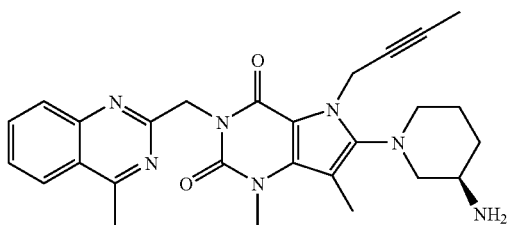 |
| (112) | 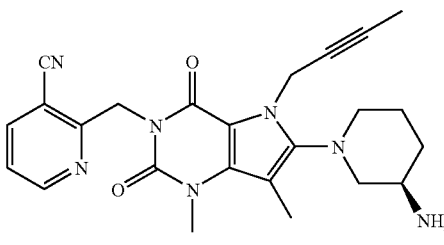 |
| Compound | Structure |
|---|---|
| (113) | 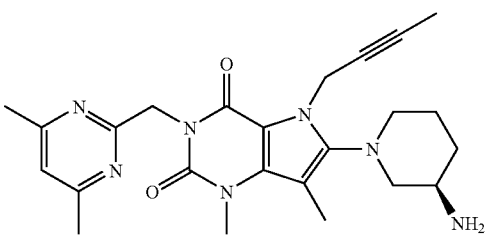 |
| (114) | 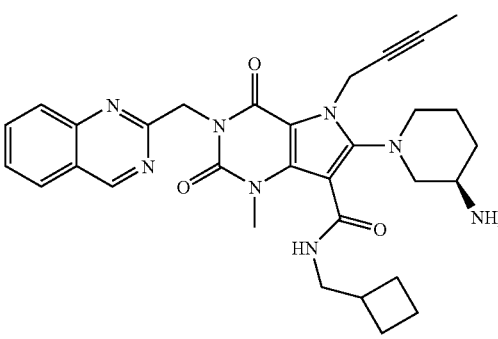 |
| (115) | 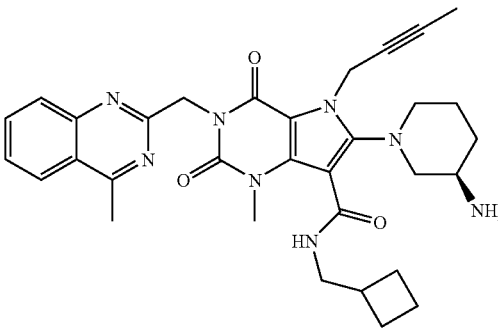 |
| (116) | 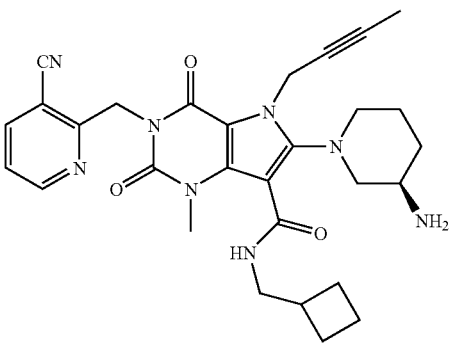 |

| Compound | Structure |
|---|---|
| (117) | 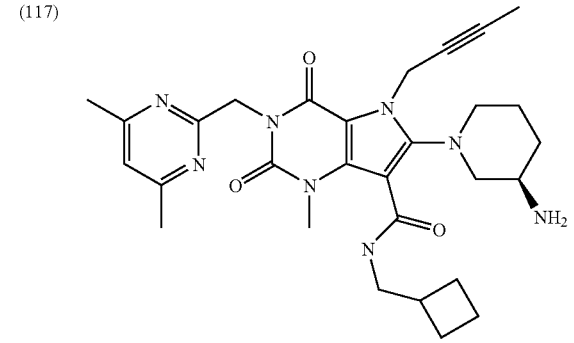 |
| (118) | 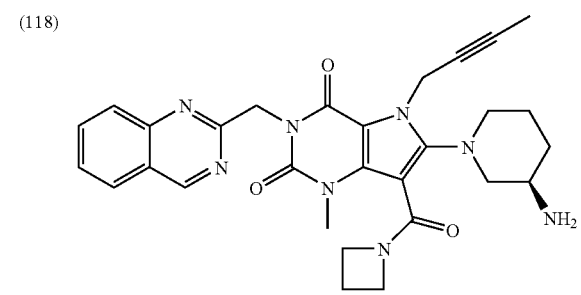 |
| (119) | 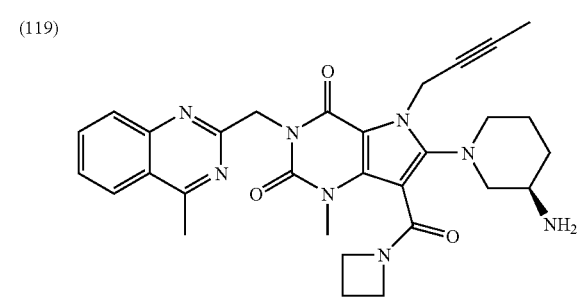 |
| (120) | 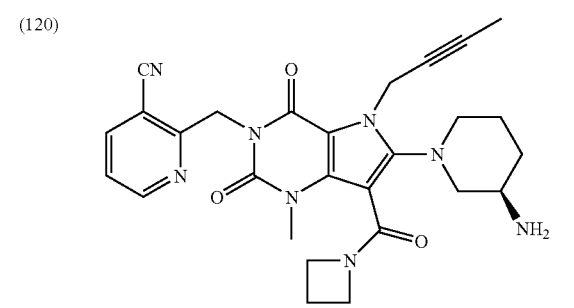 |
| (121) | 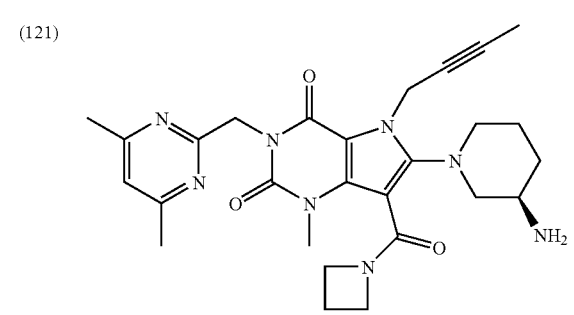 |
| Compound | Structure |
|---|---|
| (122) | 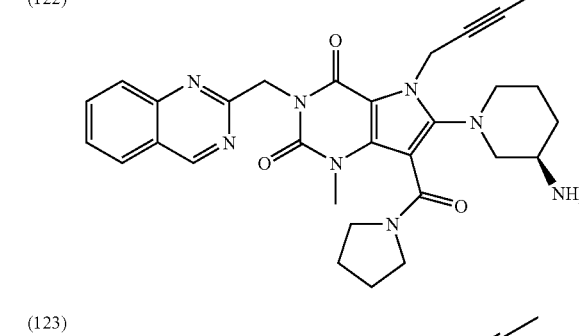 |
| (123) | 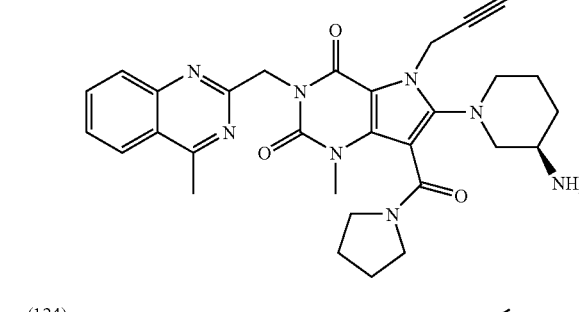 |
| (124) | 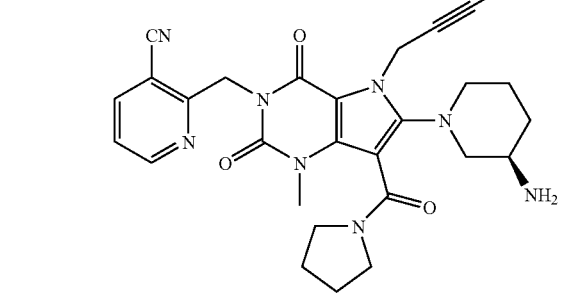 |
| (125) | 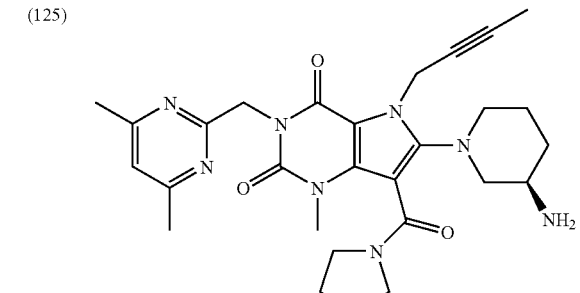 |
| (126) | 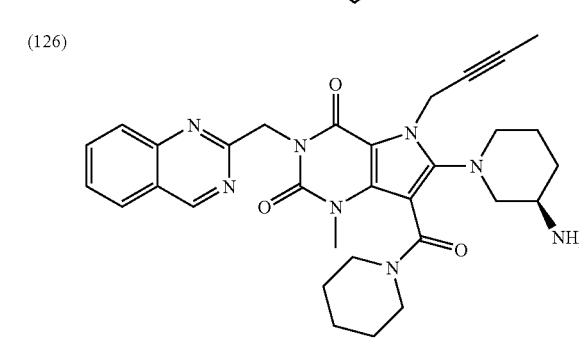 |

33

-continued

| Compound | Structure |
|---|---|
| (127) | 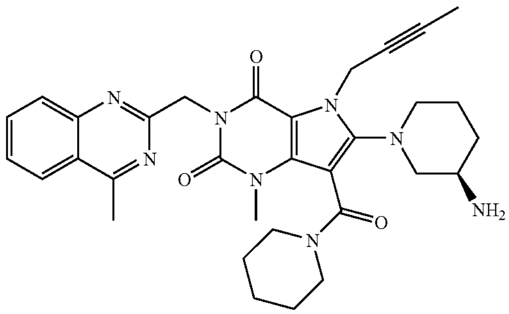 |
| (128) | 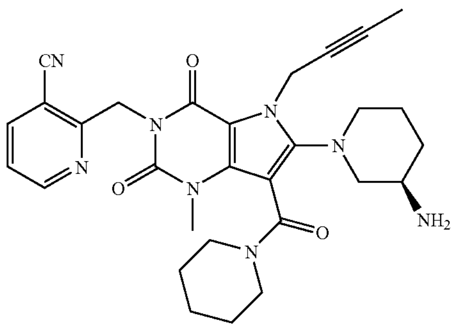 |
| (129) | 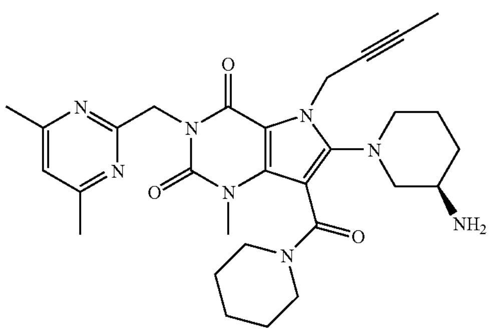 |

EXAMPLE 2

Coated Tablets Containing 75 mg of Active Substance 1 tablet core contains:

| | |
|---|---|
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation:

The active substance is mixed with calcium phosphate, corn starch, polyvinyl pyrrolidone, hydroxypropylmethylcellulose and half the specified amount of magnesium stearate. Blanks about 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape.

weight of core: 230 mg
die: 9 mm, convex

The tablet cores thus produced are coated with a film consisting essentially of hydroxypropylmethylcellulose. The finished film-coated tablets are polished with beeswax.

Weight of coated tablet: 245 mg.

EXAMPLE 3

Tablets Containing 100 mg of Active Substance

Composition:
1 tablet contains:

| | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg
Diameter: 10 mm, biplanar, facetted on both sides and notched on one side.

EXAMPLE 4

Tablets Containing 150 mg of Active Substance

Composition:
1 tablet contains:

| | |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm.

The granules, dried at 45° C., are passed through the same screen again and mixed with the specified amount of magnesium stearate. Tablets are pressed from the mixture.

Weight of tablet: 300 mg
die: 10 mm, flat

EXAMPLE 5

Hard Gelatine Capsules Containing 150 mg of Active Substance 1 capsule contains:

| | |
|---|---|
| active substance | 150.0 mg |
| corn starch (dried) | approx. 180.0 mg |
| lactose (powdered) | approx. 87.0 mg |
| magnesium stearate | 3.0 mg |
| | approx. 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg
Capsule shell: size 1 hard gelatine capsule.

EXAMPLE 6

Suppositories Containing 150 mg of Active Substance 1 suppository contains:

| | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

EXAMPLE 7

Suspension Containing 50 mg of Active Substance 100 ml of suspension contain:

| | |
|---|---|
| active substance | 1.00 g |
| carboxymethylcellulose-Na-salt | 0.10 g |
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |
| flavouring | 0.30 g |
| dist. water | ad 100 ml |

Preparation:

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution and the flavouring have been added and dissolved, the suspension is evacuated with stirring to eliminate air.

5 ml of suspension contain 50 mg of active substance.

EXAMPLE 8

Ampoules Containing 10 mg Active Substance 1 ampoule contains:

| | |
|---|---|
| active substance | 10.0 mg |
| 0.01 N hydrochloric acid | q.s. |
| double-distilled water | ad 2.0 ml |

Preparation:

The active substance is dissolved in the necessary amount of 0.01 N HCl, made isotonic with common salt, filtered sterile and transferred into 2 ml ampoules.

EXAMPLE 9

Ampoules Containing 50 mg of Active Substance 1 ampoule contains:

| | |
|---|---|
| active substance | 50.0 mg |
| 0.01 N hydrochloric acid | q.s. |
| double-distilled water | ad 10.0 ml |

Preparation:

The active substance is dissolved in the necessary amount of 0.01 N HCl, made isotonic with common salt, filtered sterile and transferred into 10 ml ampoules.

The invention claimed is:

1. A compound of formula (I)

wherein:
  R1 is ([1,5]naphthyridin-2-yl)methyl, (quinazolin-2-yl)methyl, (quinoxalin-6-yl)methyl, (4-methyl-quinazolin-2-yl)methyl, 2-cyano-benzyl, (3-cyano-quinolin-2-yl)methyl, (3-cyano-pyridin-2-yl)methyl, (4-methyl-pyrimidin-2-yl)methyl, or (4,6-dimethyl-pyrimidin-2-yl)methyl; and
  R2 is hydrogen, methyl, hydroxy, methoxy, cyano, carboxy, methoxycarbonyl, aminocarbonyl, methylaminocarbonyl, dimethylaminocarbonyl, (2-methoxyethyl)-aminocarbonyl, (2,2,2-trifluoroethyl)aminocarbonyl, cyclopropylaminocarbonyl, cyclobutylaminocarbonyl, (cyclopropylmethyl)aminocarbonyl, (cyclobutylmethyl)-aminocarbonyl, azetidin-1-ylcarbonyl, pyrrolidin-1-ylcarbonyl, piperidin-1-ylcarbonyl or morpholin-4-ylcarbonyl; or
  a tautomer, enantiomer, diastereomer, mixture or salt thereof.

2. The compound according to claim 1 of formula (IA) or (IB)

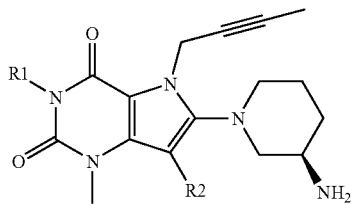
(IA)

or (IB)

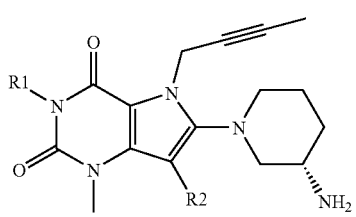
(IB)

or a tautomer or salt thereof.

3. A compound of formula (II)

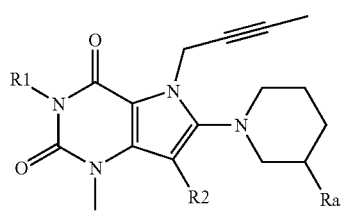
(II)

wherein:
R1 is ([1,5]naphthyridin-2-yl)methyl, (quinazolin-2-yl) methyl, (quinoxalin-6-yl)methyl, (4-methyl-quinazolin-2-yl)methyl, 2-cyano-benzyl, (3-cyano-quinolin-2-yl)methyl, (3-cyano-pyridin-2-yl)methyl, (4-methyl-pyrimidin-2-yl)methyl, or (4,6-dimethyl-pyrimidin-2-yl)methyl;

R2 is hydrogen, methyl, hydroxy, methoxy; cyano, carboxy, methoxycarbonyl, aminocarbonyl, methylaminocarbonyl, dimethylaminocarbonyl, (2-methoxyethyl)-aminocarbonyl, (2,2,2-trifluoroethyl) aminocarbonyl, cyclopropylaminocarbonyl, cyclobutylaminocarbonyl, (cyclopropylmethyl)aminocarbonyl, (cyclobutylmethyl)-aminocarbonyl, azetidin-1-ylcarbonyl, pyrrolidin-1-ylcarbonyl, piperidin-1-ylcarbonyl or morpholin-4-ylcarbonyl; and Ra denotes an amino group protected by a protective group.

4. The compound according to claim 1, characterised in that the compound is a physiologically acceptable salt with an inorganic or organic acid.

5. A medicament containing a compound according to claim 1 and one or more inert carriers and/or diluents.

6. A process for preparing the compound according to claim 1 or a salt thereof, comprising deprotecting a compound of formula (II)

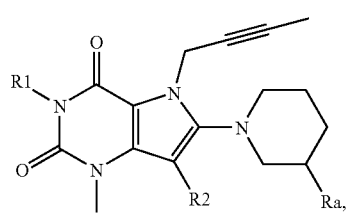
(II)

or a salt thereof, wherein
R1 and R2 are as defined in claim 1; and
Ra denotes an amino group protected by a protective group.

7. The process according to claim 6, characterised in that the compound of formula (I) or salt thereof thus obtained is resolved into an enantiomer or diastereomer thereof.

8. The process according claim 6, characterised in that the compound of formula (I) or salt thereof thus obtained with an inorganic or organic acid is converted into a physiologically acceptable salt thereof.

9. A process for the treatment of type II diabetes mellitus, comprising administering to a patient in need thereof a therapeutically effective amount of the compound of claim 1 or a salt thereof.

* * * * *